US006251389B1

(12) United States Patent
Magna et al.

(10) Patent No.: US 6,251,389 B1
(45) Date of Patent: Jun. 26, 2001

(54) HUMAN NUCLEOTIDE PYROPHOSPHOHYDROLASE-2

(75) Inventors: Holly Magna, Niantic; Paul Schaffer, Groton; Michael Lawton, Westbrook; Sue Yocum, Baltic; Peter Mitchell, Mystic; Nancy Hutchinson, Old Lyme, all of CT (US); Lynn E. Murry, Portola Valley, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/429,516

(22) Filed: Oct. 28, 1999

Related U.S. Application Data

(62) Division of application No. 08/996,083, filed on Dec. 22, 1997.

(51) Int. Cl.[7] .............................. A61K 38/46; C12N 9/12; C12Q 1/42; C07H 21/04
(52) U.S. Cl. ..................... 424/94.6; 435/195; 435/252.3; 435/320.1; 435/21; 536/23.2; 530/350
(58) Field of Search .............................. 424/94.6; 435/21, 435/195, 252.3, 320.1; 536/23.2; 530/350

(56) References Cited

PUBLICATIONS

Swan, A. et al., "Submicroscopic crystals in osteoarthritic synovial fluids" *Ann.Rheum.Dis.* (1994) 53:467–470.
Lohmander, L. S. et al., "Metalloproteinases, Tissue Inhibitor, and Proteoglycan Fragments in Knee Synovial Fluid in Human Osteoarthritis" *Arthritis Rheum.* (1993) 36:181–189.
Ryan, L.M. et al., "Adenosine Triphosphate Levels in Human Plasma" *J. Rheumatol.* (1996) 23:214–219.
Park, W. et al., "Inorganic Pyrophosphate Generation from Adenosine Triphosphate by Cell–Free Human Synovial Fluid" *J. Rheumatol.* (1996) 23: 665–671.
Derfus, B. A. et al., "Articular Cartilage Vesicles Generate Calcium Pyrophosphate Dihydrate–Like Crystals In Vitro" *Arthritis Rheum.* (1992) 365:231–240.
Cardenal, A. et al., "Identification of a Nucleotide Pyrophosphohydrolase From Articular Tissues In Human Serum" *Arthritis Rheum.* (1996) 39:252–256.
Cardenal, A. et al., "Specificity of a Porcine 127–KD Nucleotide Pyrophosphohydrolase for Articular Tissues" *Arthritis Rheum.* (1996) 39:245–251.
Masuda, I. et al., "A unique ectonucleotide pyrophosphohydrolase associated with porcine chondrocyte–derived vesicles" *J.Clin.Invest.* (1995) 95:699–704 (abstract attached).
Masuda, I. et al., "Molecular cloning and expression of a porcine chondrocyte nucleotide pyrophosphohydrolase" *Gene* (1997) 197 :277–287 (abstract attached).
Lorenzo, P. et al., "Cloning and Deduced Amino Acid Sequence of a Novel Cartilage Protein (CILP) Identifies a Proform Including a Nucleotide Pyrophosphohydrolase", *J. Biol. Chem.* 273: 23469–23475 (1998).
Suggs, S. V. et al., "Use of synthetic oligonucleotides as hybridization probes: Isolation of cloned cDNA sequences for human $\beta_2$–microglobulin" *Proc. Natl. Acad. Sci. USA*, 78: 6613–6617 (1981).

*Primary Examiner*—Tekchand Saidha
(74) *Attorney, Agent, or Firm*—Incyte Genomics, Inc.

(57) ABSTRACT

The invention provides a human nucleotide pyrophosphohydrolase-2 (NTPPH-2) and polynucleotides which identify and encode NTPPH-2. The invention also provides expression vectors, host cells, agonists, antibodies and antagonists. The invention also provides methods for treating disorders associated with expression of NTPPH-2.

4 Claims, 16 Drawing Sheets

```
5' GCC CGA GCA CGC CGC GGA GCC CGG ACC TCC CTC GGA CGC TCT GCC CCG GCC ATG
                                                                        M
    9           18          27          36          45          54

GCG TCG CTG CTG CCA CTG CTC TGT GTC GCT GCG TCT GCC CAC CTG GCG GGG
 A   S   L   L   P   L   L   C   V   A   A   S   A   H   L   A   G
    63          72          81          90          99          108

GCC CGA GAC GCC ACC CCC ACC GAG CCA ATG GCG ACT GCA CTG GGC CTG GAA
 A   R   D   A   T   P   T   E   P   M   A   T   A   L   G   L   E
    117         126         135         144         153         162

AGA CGG TCC GTG TAC ACC GGC CAG CCC TCA CCA GCC CTG GAG GAC TGG GAA GAG
 R   R   S   V   Y   T   G   Q   P   S   P   A   L   E   D   W   E   E
    171         180         189         198         207         216

GCC GAG TGG ACG TCC TGG TTC AAC GTG GAC GCC CAC CCC GGA GGC GAC GGC GAC
 A   E   W   T   S   W   F   N   V   D   A   H   P   G   G   D   G   D
    225         234         243         252         261         270

TTC GAG AGC CTG GCT GCC ATC CGC TTC TAC TAC GAC ACG GAC TGG GCC CGC GTG TGC CCG
 F   E   S   L   A   A   I   R   F   Y   Y   D   T   D   W   A   R   V   C   P
    279         288         297         306         315         324

CGA CCG CTG GCG CTG GAG GCG CGC ACC ACC CGC CTG CCG TCC GCC GTC
 R   P   L   A   L   E   A   R   T   T   R   L   P   S   A   V
    333         342         351         360         369         378
```

FIGURE 1A

```
387                 396         405         414         423         432
GGC GAG CGC GTG CAC TTG AAC CCC ACG CGC GGC TTC TGG TGC CTC AAC CGC GAG
 G   E   R   V   H   L   N   P   T   R   G   F   W   C   L   N   R   E 441                 450         459         468         477         486
CAA CCG CGT GGC CGC CGC TGC TCC AAC TAC CAC GTG CGC TTC CGC TGC CCA CTA
 Q   P   R   G   R   R   C   S   N   Y   H   V   R   F   R   C   P   L 495                 504         513         522         531         540
GAA GCC TCG TGG GGC GCG TGG GGC CCG TGG GGT CCC TGC TCG GGG AGC TGT GGG
 E   A   S   W   G   A   W   G   P   W   G   P   C   S   G   S   C   G 549                 558         567         576         585         594
CCA GGC CGT CGC TTG CGC CGC CAC TGC CCA AGC CCC GCT TCG GGG GAT GCG TGT
 P   G   R   R   L   R   R   H   C   P   S   P   A   S   G   D   A   C 603                 612         621         630         639         648
CCC GGG CGT CCT CTG GAG GCG CAG AAG TGC GTG CGG CCT CGG GGC TGT CCA GGG TGC
 P   G   R   P   L   E   A   Q   K   C   V   R   P   R   G   C   P   G   C 657                 666         675         684         693         702
AGC CTT GAC ACC TGT GAA TGC CCG GAC CAC ATC CTC CTG GGC TCG GTG GTC ACC
 S   L   D   T   C   E   C   P   D   H   I   L   L   G   S   V   V   T 711                 720         729         738         747         756
CCA TCT GGG CAA CCA CTG CTA GGA GCC AGG GTC TCC CTG CGA GAC CAG CCT GGC
 P   S   G   Q   P   L   L   G   A   R   V   S   L   R   D   Q   P   G
```

FIGURE 1B

```
765         774         783         792         801         810
ACT GTG GCC ACC AGC GAT GCT CAC GGA ACC TTC CGG GTG CCT GGT GTC TGT GCT
 T   V   A   T   S   D   A   H   G   T   F   R   V   P   G   V   C   A 819         828         837         846         855         864
GAC AGC CGC GCC AAC ATC AGG GCC CAG ATG GAT GGC TTC TCT GCA GGG GAG GCC
 D   S   R   A   N   I   R   A   Q   M   D   G   F   S   A   G   E   A 873         882         891         900         909         918
CAG GCC CAG GCC AAC GGA TCC ATC TCT GTG GTC ACC ATC ATC CTT GAT AAG TTG
 Q   A   Q   A   N   G   S   I   S   V   V   T   I   I   L   D   K   L 927         936         945         954         963         972
GAG AAG CCG TAC CTG GTG AAA CAC CCT GAG TCC CGA GTG CGA GAG GCT GGC CAG
 E   K   P   Y   L   V   K   H   P   E   S   R   V   R   E   A   G   Q 981         990         999        1008        1017        1026
AAT GTG ACT TTC TGC AAA GCC ACC CTG GAC AGG CGA GTG CCC ATG CCC AAG TCC
 N   V   T   F   C   K   A   T   L   D   R   R   V   P   M   P   K   S 1035        1044        1053        1062        1071        1080
TGG TTC CAC AAT GGG ACC CTG CTG GAC AGG CGA GCT CAT GGG TAC GGG GCC CAC
 W   F   H   N   G   T   L   L   D   R   R   A   H   G   Y   G   A   H 1089        1098        1107        1116        1125        1134
CTG GAG CTS CGG GGA CTG CGC CCA GAC CAG GCT GGC ATC TAC CAC TGC AAG GCA
 L   E   L   R   G   L   R   P   D   Q   A   G   I   Y   H   C   K   A
```

FIGURE 1C

```
                1143        1152        1161        1170        1179        1188
            TGG AAT GAG GCG GGT GCC GTG CGC TCG GGC ACT GCC CGG CTC ACT GTA CTT GCC
             W   N   E   A   G   A   V   R   S   G   T   A   R   L   T   V   L   A 1197        1206        1215        1224        1233        1242
            CCA GGC CAG CCA GCC TGC GAC CCC CGG CGA GAG TAC CTG ATC AAG CTC CCT
             P   G   Q   P   A   C   D   P   R   R   E   Y   L   I   K   L   P 1251        1260        1269        1278        1287        1296
            GAG GAC TGT GGT CAG CCA GGT AGT GGC CCT GCC TAC CTG GAT GTG GGC CTC TGT
             E   D   C   G   Q   P   G   S   G   P   A   Y   L   D   V   G   L   C 1305        1314        1323        1332        1341        1350
            CCC GAC ACC CGC TGC CCC AGC CTG GCA GGC TCC AGC CCC CGC TGC GGG GAC GCC
             P   D   T   R   C   P   S   L   A   G   S   S   P   R   C   G   D   A 1359        1368        1377        1386        1395        1404
            AGC TCC CGC TGC TGC TCT GTG CGC CGT CTG GAG AGA AGG GAG ATT CAC TGC CCT
             S   S   R   C   C   S   V   R   R   L   E   R   R   E   I   H   C   P 1413        1422        1431        1440        1449        1458
            GGC TAC GTC CTC CCA GTG AAG GTG GTG GCA GAG TGT TGC TGC CAG AAG TGT CTG
             G   Y   V   L   P   V   K   V   V   A   E   C   C   C   Q   K   C   L 1467        1476        1485        1494        1503        1512
            CCC CCT CGG GGG CTG GTC CGT GTT GTG GCT GCT GAC TCC GGG GAG CCG
             P   P   R   G   L   V   R   V   V   A   A   D   S   G   E   P
```

FIGURE 1D

```
      1521              1530              1539             1548              1557          1566
CTA CGC TTC GCC AGG ATT CTG CTG GGC CAG GAG CCC ATC GGC TTC ACC GCC TAC
 L   R   F   A   R   I   L   L   G   Q   E   P   I   G   F   T   A   Y 1575              1584              1593             1602              1611          1620
CAG GGC GAC TTT ACC ATT GAG GTG CCG CCC TCC ACC CAG CGG CTG GTG ACT
 Q   G   D   F   T   I   E   V   P   P   S   T   Q   R   L   V   T 1629              1638              1647             1656              1665          1674
TTT GTG GAC CCC AGC GGT GAG TTC ATG GAC GCT GTC CGG GTC TTG CCT TTT GAT
 F   V   D   P   S   G   E   F   M   D   A   V   R   V   L   P   F   D 1683              1692              1701             1710              1719          1728
CCT CGA GGT GCC GGC GTG TAC CAC GAG GTC AAG GCC ATG CGG AAG AAA GCC CCG
 P   R   G   A   G   V   Y   H   E   V   K   A   M   R   K   K   A   P 1737              1746              1755             1764              1773          1782
GTC ATT TTA CAT ACC AGC AGC CAG AGC AAC ACG ATC CCC CTG GGC GAG CTG GAA GAT
 V   I   L   H   T   S   Q   S   N   T   I   P   L   G   E   L   E   D 1791              1800              1809             1818              1827          1836
GAG GCG CCC CTG GGC GAG CTG GTC CCT CTG GGC GCT TTC CGC AGA GCC GAC
 E   A   P   L   G   E   L   V   P   L   G   A   F   R   R   A   D 1845              1854              1863             1872              1881          1890
GGC AAA CCC TAC TCG GGG CCT GTG GAG GCC CGG GTG ACG TTC GTG GAC CCC CGA
 G   K   P   Y   S   G   P   V   E   A   R   V   T   F   V   D   P   R
```

FIGURE 1E

```
                1899      1908      1917      1926      1935      1944
                GAC CTC ACC TCG GCG GCG TCT GCC CCC AGT GAC CTG CGC TTC GTG GAC AGC GAC
                 D   L   T   S   A   A   S   A   P   S   D   L   R   F   V   D   S   D 1953      1962      1971      1980      1989      1998
                GGC GAG CTG GCT CCA CTG CGC ACC TAC GGC ATG TTC TCC GTG GAC CTC CGT GCG
                 G   E   L   A   P   L   R   T   Y   G   M   F   S   V   D   L   R   A 2007      2016      2025      2034      2043      2052
                CCC GGC TCC GCG GAG CAG CTG CAG GGG CCG GTG GCC GTG CGG GTG GCC GCC
                 P   G   S   A   E   Q   L   Q   G   P   V   A   V   R   V   A   A 2061      2070      2079      2088      2097      2106
                AGC CAG ATC CAC ATG CCA GGC CAC GTG GAG GCC CTC AAG CTG TGG TCG CTG AAC
                 S   Q   I   H   M   P   G   H   V   E   A   L   K   L   W   S   L   N 2115      2124      2133      2142      2151      2160
                CCC GAG ACC GGC TTG TGG GAG GAG AGC GGC TTC CGG CGC GAG GGG TCC TCG
                 P   E   T   G   L   W   E   E   S   G   F   R   R   E   G   S   S 2169      2178      2187      2196      2205      2214
                GGC CCC CGG GTG CGC GAG GAG CGG GTC TTC CTG GTG GGC AAC GTG GAG ATC
                 G   P   R   V   R   E   E   R   V   F   L   V   G   N   V   E   I 2223      2232      2241      2250      2259      2268
                CGG GAG CGG CTG TTC AAT CTG GAC GTG CCT GAG CGC CGC TGC TTC GTG
                 R   E   R   L   F   N   L   D   V   P   E   R   R   C   F   V
```

FIGURE 1F

```
         2277              2286              2295              2304              2313              2322
AAG GTG CGC GCC TAC GCC AAC GAC AAG TTC ACC CCC AGC GAG CAG GTG GAG GGC
 K   V   R   A   Y   A   N   D   K   F   T   P   S   E   Q   V   E   G
         2331              2340              2349              2358              2367              2376
GTG GTG ACG CTG GTC AAT CTG GAG CCC GCC CCC GGC TTC TCC GCC AAC CCC
 V   V   T   L   V   N   L   E   P   A   P   G   F   S   A   N   P
         2385              2394              2403              2412              2421              2430
CGT GCC TGG GGC CGC TTT GAC AGC GCG GTC ACC GGC CCC AAT GGC GCC TGC CTC
 R   A   W   G   R   F   D   S   A   V   T   G   P   N   G   A   C   L
         2439              2448              2457              2466              2475              2484
CCC GCC TTC TGC GAC GAG GAC AGG CCA GAC GCC TAC ACC GCC CTG GTC ACC GCC
 P   A   F   C   D   E   D   R   P   D   A   Y   T   A   L   V   T   A
         2493              2502              2511              2520              2529              2538
ACC CTG GGC GGC GAG GAG CTG GAG CCG GCC CCT TCC TTG CCC CGC CCA CTC CCG
 T   L   G   G   E   E   L   E   P   A   P   S   L   P   R   P   L   P
         2547              2556              2565              2574              2583              2592
GCC ACC GTG GGC GTC ACC CAG CCC TAC CTG GAC AGG CTG GGG TAC CGT CGG ACG
 A   T   V   G   V   T   Q   P   Y   L   D   R   L   G   Y   R   R   T
         2601              2610              2619              2628              2637              2646
GAC CAC GAC GAT CCC GCC TTC AAG CGT AAC GGC TTC CGC ATC AAC CTC GCC AAG
 D   H   D   D   P   A   F   K   R   N   G   F   R   I   N   L   A   K

FIGURE 1G
```

```
            2655           2664           2673           2682           2691           2700
CCC AGG CCA GGT GAC CCC GCC GAG CCC AAT GGG CCT GTG TAC CCG TGG CGC AGC
 P   R   P   G   D   P   A   E   P   N   G   P   V   Y   P   W   R   S
            2709           2718           2727           2736           2745           2754
CTG CGG GAA TGC CAG GGG GCC CCG GTG ACT GCC AGC CAC TTC CGC TTC GCC AGG
 L   R   E   C   Q   G   A   P   V   T   A   S   H   F   R   F   A   R
            2763           2772           2781           2790           2799           2808
GTG GAG GCG GAC AAG TAC GAG TAC AAC GTG GTC GTC CCC TTC CGA GAG GGC ACA CCT
 V   E   A   D   K   Y   E   Y   N   V   V   P   F   R   E   G   T   P
            2817           2826           2835           2844           2853           2862
GCC TCC TGG ACT GGC GAT CTC CTG GCC TGG TGG CCC AAC CCG CAG GAG TTC CGG
 A   S   W   T   G   D   L   L   A   W   W   P   N   P   Q   E   F   R
            2871           2880           2889           2898           2907           2916
GCC TTC CTC AAG GTG AAG ATC CAG GGT CCC CAG GAG TAT ATG GTC CGC TCC
 A   F   L   K   V   K   I   Q   G   P   Q   E   Y   M   V   R   S
            2925           2934           2943           2952           2961           2970
CAC AAC GCA GGG GGC AGC CAC CCA CGC ACC CGC GGC CAG CTC TAC GGA CTT CGG
 H   N   A   G   G   S   H   P   R   T   R   G   Q   L   Y   G   L   R
            2979           2988           2997           3006           3015           3024
GAT GCC CGG AGT GTG CGA GAC CCC GAG CGT CCG GGC ACC TCG GCA GCC TGC GTG
 D   A   R   S   V   R   D   P   E   R   P   G   T   S   A   A   C   V
```

FIGURE 1H

```
     3033            3042       3051            3060            3069            3078
GAG TTC AAG TGC AGC GGG ATG CTG TTC GAC CAG CGG CAG GTG GAC AGG ACG CTG
 E   F   K   C   S   G   M   L   F   D   Q   R   Q   V   D   R   T   L 3087            3096       3105            3114            3123            3132
GTG ACC ATT ATG CCC CAG GGC AGC TGC CGG CGC GTG GCC GTC AAC GGA CTC CTT
 V   T   I   M   P   Q   G   S   C   R   R   V   A   V   N   G   L   L 3141            3150       3159            3168            3177            3186
CGG GAT TAC CTG ACC CGG CAC CCC CCA CCG GTG CCC GCG GAG GAC CCA GCT GCC
 R   D   Y   L   T   R   H   P   P   P   V   P   A   E   D   P   A   A 3195            3204       3213            3222            3231            3240
TTC TCC ATG CTG GCC CCC CTA GAC CCT CTG GGC CAC AAC TAT GGC GTC TAC ACT
 F   S   M   L   A   P   L   D   P   L   G   H   N   Y   G   V   Y   T 3249            3258       3267            3276            3285            3294
GTC ACT GAC CAG AGC CCA CGC TTG GCC AAG GAG ATC GCC ATT GGC CGC TGC TTT
 V   T   D   Q   S   P   R   L   A   K   E   I   A   I   G   R   C   F 3303            3312       3321            3330            3339            3348
GAT GGT TCC TCT GAC CAG GGY TTC TCC AGA GAG ATG AAG GCT GAT GCC GGC ACA GCC
 D   G   S   S   D   Q   G   F   S   R   E   M   K   A   D   A   G   T   A 3357            3366       3375            3384            3393            3402
GTC ACC TTC CAG TGC CGG GAG CCA CCG GCC CGA CCC AGC CTC TTC CAG AGG
 V   T   F   Q   C   R   E   P   P   A   G   R   P   S   L   F   Q   R
```

FIGURE 1I

```
      3411            3420            3429            3438            3447            3456
CTG CTG GAG TCC CCG GCG ACA GCA CTT GGT GAC ATC CGC AGG GAG ATG AGC GAG
 L   L   E   S   P   A   T   A   L   G   D   I   R   R   E   M   S   E 3465            3474            3483            3492            3501            3510
GCG GCG CAG GCA CAG GCC CGG GCC TCA GGT CCC CTC CGC ACC CGC CGG GGT AGG
 A   A   Q   A   Q   A   R   A   S   G   P   L   R   T   R   R   G   R 3519            3528            3537            3546            3555            3564
GTC CGG CAG TGA CCT GGG CAG GGG CCT CGC TTT CCC ACC TCC CTC CAG ACT CCT
 V   R   Q 3573            3582            3591            3600            3609            3618
TTG ACC CCA GGA AGT TTT GCC CCT TCT TCT CCA GAC AGC CCC CTC CCC AGG 3627            3636            3645            3654            3663            3672
TGT CTG GGT CCC CTT TCC CGC CCC TTT CCA GAA CTC AGA GTC AGA CAA GAA CCC 3681            3690            3699            3708            3717            3726
AGA GCA TCC GAT GGT AGA AAC ACC AGG AAG ACA ATT GTT GCT GTG TGG TAT GGA 3735            3744            3753            3762            3771            3780
ATG GAG TTT GCG GTG ACT CTG GGG CCA GCA CCC AGG GGA CGA CGT TCA ACC CTA 3789            3798            3807            3816            3825            3834
GCC TGA AGG GAC CCG CTC CCA GCT CAG AAG CCG TCT CTG ACT TCT CGT GCG TAT
```

FIGURE 1J

```
      3843            3852            3861            3870            3879            3888
TTT GAC CCT GAT TTC AAT CTT CTA CCC TTG GGA GTT CTG GCG TTT GGC ACA AAG 3897            3906            3915            3924            3933            3942
TCC CCT CTG CCT GTT TGG AGC TCA GTG CTA GAC CAG GTC CCC TGC CCC GAG CTT 3951            3960            3969            3978            3987            3996
TGT TTT TGG GGT TAT TTA AAA CAA AGT GTG GGG AGC TGG TTG TGG GTG TGA 4005            4014            4023            4032            4041            4050
GTG GGG GTG TGG GGT CCA GGC TGG GCC CAG TGA AAA GGA GGA AGG GGT TCC CAT
 V   G   V   W   G   P   G   W   A   Q 4059            4068            4077            4086            4095            4104
GCG GGG GAG GCT CTG GGG CTG AGG GGA ACA ATT CTC ACG TGT TTG GTG CTT AGA 4113            4122            4131            4140            4149            4158
GAC CTG CCC GGG GCG TTG GGC AGG CCC TCC GGG TGA ATT AAA AAT GCT TTA 4167            4176
TTT CCA AAA AAA AAA AAA AAA NAA A 3'
```

FIGURE 1K

```
  1   MAS----LLPLLCLCVVAAHLAGARDATPTEEPMATALGL        NTPPH-2
  1   MVGTKAWVFSFLVL-EVTSVLG--RQTMLTQSVRRVQPGK        NTPPH-1

37   ERRSVYTGQPSPALEDWEEASEWTSWFNVDHPGGDGDFES        NTPPH-2
 38   KNPSIFA-KPADTLE---SPGEWTTWFNIDYPGGKGDYER        NTPPH-1

77   LAAIRFYYGPARVCPRPLALEARTTDWALPSAVGERVHLN        NTPPH-2
 74   LDAIRFYYG-DRVCARPLRLEARTTDWTPAGSTGQVVHGS        NTPPH-1

117   PTRGFWCLNREQPRGRRCSNYHVRFRCP-----LEASW          NTPPH-2
113   PREGFWCLNREQRPGQNCSNYTVRFLCPPGSLRRDTERIW        NTPPH-1

150   GAWGPWGPCSGSCGP-GRRLRRRHCPSPAGDACPGRPLEA        NTPPH-2
153   SPWSPWSKCSAACGQTGVQTRTRICLAEMVSLCSEASEEG        NTPPH-1

189   QKCVRPRCPGCSL-----DTCECPDHILLGSVVT              NTPPH-2
193   QHCMGQDDCTACDLTCPMGQVNADCDACMCQDFMLHGAVSL       NTPPH-1

218   PSGQPLLGARVSLRDQ-PGTVATSDAHGTFRVPGVCADSR        NTPPH-2
233   PGGAPASGAAIYLLTKTPKLLTQTDSDGRFRIPGLCPDGK        NTPPH-1

257   ANIRAQMDGFSA-GEAQAQANGSISVVTILDKLEKPYLV         NTPPH-2
273   SILKITKVKFAPIVLTMPKTSLKAATIKAEFVRAETPYMV        NTPPH-1

296   KHPESRVREAGQNVTFCCKASGTPMPKKYSWFHNGTLLDR        NTPPH-2
313   MNPETKARRAGQSVSLCCKATGKPRPDKYFWYHNDTLLDP        NTPPH-1

336   RAHGYGAHLELRGLRPDQAGIYHCKAWNEAGAVRSGTARL        NTPPH-2
353   SLYKHESKLVLRKLQQHQAGEYFCKAQSDAGAVKSKVAQL        NTPPH-1
```

FIGURE 2A

```
376  TVLAPGQPACDPRPREYLIKLPEDCGQPGSGPAYLDVGLC  NTPPH-2
393  IVIASDETPCNPVPESYLIIRLPHDCFQNATNSFYYDVGRC NTPPH-1

416  PDTRCPSLAGSSPRCGDASSRCCSVRRLERREIHCPGYVL  NTPPH-2
433  PVKTCAGQQDNGIRDAVQNCCGISKTEEREIQCSGYTL    NTPPH-1

456  PVKVVAECGCQKCLPPRGLVRGRVVAADSGEPLRFARILL  NTPPH-2
473  PTKVAKECSCQRCTETRSIVRGRVSAADNGEPMRFGHVYM  NTPPH-1

496  GQEPIGFTAYQGDFTIEVPPSTQRLVVTFVDPSGEFMDAV  NTPPH-2
513  GNSRVSMTGYKGTFTLHVPQDTERLVLTFVDRLQKFVNTT  NTPPH-1

536  RVLPFDPRGAGVYHEVKAMRKKAPVILHTSQSNTIPLGEL  NTPPH-2
553  KVLPFNKKGSAVFHEIKMLCRKEPITLEAMETNIIPLGEV  NTPPH-1

576  EDEAPLGELVLPSGAFRRADGKPYSGPVEARVTFVDPRDL  NTPPH-2
593  VGEDPMAELEIPSRSFYRQNGEPYIGKVKASVTFLDPRNI  NTPPH-1

616  TSAASAPSDLRFVDSDGELAPLRTYGMFSVDLRAPGSAEQ  NTPPH-2
633  STATAAQTDLNFINDEGDTFPLRTYGMFSVDFRDEVTSEP  NTPPH-1

656  LQVGPVAVRVAASQIHMPGHVEALKLWSLNPETGLWEEES  NTPPH-2
673  LNAGKVKVHLDSTQVKMPEHISTVKLWSLNPDTGLWEEEG  NTPPH-1

696  GFRREGSSGPRVRREERVFLVGNVEIRERRLFNLDVPERR  NTPPH-2
713  DFKFE--NQRRNKREDRTFLVGNLEIRERRLFNLDVPESR  NTPPH-1

736  RCFVKVRAYANDKFTPSEQVEGVVVTLVNLEPAPGFSANP  NTPPH-2
751  RCFVKVRAYRSERFLPSEQIQGVVISVINLEPRTGFLSNP  NTPPH-1
```

FIGURE 2B

```
776                                                                                                    NTPPH-2
      R A W G R F D S A V T G P N G A C L P A F C D A D R P D A Y T A L V T A T L G G
791   R A W G R F D S V I T G P N G A C V P A F C D D Q S P D A Y S A Y V L A S L A G                NTPPH-1

816   E E L E P A P S L P R P L P A T V G V T Q P Y L D R L G Y R R T D H D D P A F K                NTPPH-2
831   E E L Q A V E S S P K F N P N A I G V P Q P Y L N K L N Y R R T D H E D P R V K                NTPPH-1

856   R N G F R I N L A K P R P G D P A E A N G P V Y P W R S L R E C Q G A P V T A S                NTPPH-2
871   K T A F Q I S M A K P R P E N S A E E S N G P I Y A F E N L R A C E E A P P S A A              NTPPH-1

896   H F R F A R V E A D K Y E Y N V V P F R E G T P A S W T G D L L A W P N P Q E                  NTPPH-2
911   H F R F Y Q I E G D R Y D Y N T V P F N E D D P M S W T E D Y L A W P K P M E                  NTPPH-1

936   F R A C F L K V K I Q G P Q E Y M V R S H N A G G S H P R T R G Q L Y G L R D A                NTPPH-2
951   F R A C Y I K V K I V G P L E V N V R S R N M G G T H R R T V G K L Y G I R D V                NTPPH-1

976   R S V R D P E R P G T S A A C V E F K C S G M L F D Q R Q V D R T L V T I M P Q                NTPPH-2
991   R S T R D R D Q P N V S A A C L E F K C S G M L Y D Q D R V D R T L V K V I P Q                NTPPH-1

1016  G S C R R V A V N G L L R D Y L T R H P P P V P A E D P A A F S M L A P L D P L                NTPPH-2
1031  G S C R R A S V N P M L H E Y L V N H L P L A V N N D T S E Y T M L A P L D P L                NTPPH-1

1056  G H N Y G V Y T V T D Q S P R L A K E I A I G R C F D G S S D G F S R E M K A D                NTPPH-2
1071  G H N Y G I Y T V T D Q D P R T A K E I A L G R C F D G T S D G S S R I M K S N                NTPPH-1

1096  A G T A V T F Q C R E P P A G R P S L F Q R L L E S P A - - T A L G D I R - - -                NTPPH-2
1111  V G V A L T F N C V E R Q V G R Q S A F Q Y L Q S T P A Q S P A A G T V Q G R V                NTPPH-1

1131  - - R E M S E A A Q A Q A R A S G P L - - - - R T R R G R V R Q                                NTPPH-2
1151  P S R R Q Q R A S R G G Q R Q S G V V A S L R F P R I V A Q Q P L I N                          NTPPH-1

FIGURE 2C
```

HUMAN NUCLEOTIDE PYROPHOSPHOHYDROLASE-2

This application is a divisional application of U.S. application Ser. No. 08/996,083, filed Dec. 22, 1997.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

This invention relates to nucleic acid and amino acid sequences of a human nucleotide pyrophosphohydrolase-2 and to the use of these sequences in the diagnosis, prevention, and treatment of arthropathies, immunological disorders, and cancers.

BACKGROUND

Calcium pyrophosphate dihydrate (CPPD) deposition disease is an arthropathy characterized by the accumulation of CPPD crystals in articular tissues including synovial fluid. CPPD crystals contribute significantly to the chronic pain and tissue damage of joint degeneration, and in vitro they induce neutrophil activation and fibroblast and chondrocyte mitogenesis as well as the production of matrix metalloproteinases (MMP) and prostaglandins. CPPD deposition is associated with acute inflammatory episodes (pseudogout), chronic arthritis, and degenerative joint disease. Although only about 10% of the CPPD patient population ever experience acute inflammatory attacks, the majority of patients with chronic arthritis of the large joints have CPPD deposition. CPPD crystals play a significant role in arthritic disease progression. Synovial fluids containing CPPD crystals sampled from patients with degenerative joint disease have high concentrations of cartilage fragments and MMPs, e.g., collagenase and stromelysin. (Swan, A. B. et al. (1994) Ann. Rheum. Dis. 53:467–470; Lohmander, L. S. et al. (1993) Arthritis. Rheum. 36:181–189.)

Deposition of CPPD crystals appears to be related to excess levels of extracellular calcium, pyrophosphate (PPi), or both. Whereas elevated calcium levels do not appear to be a major contributing factor to CPPD deposition in joints, elevated PPi levels have been observed in the synovial fluids from patients with CPPD deposition. Synovial fluid PPi may be produced by joint tissues because PPi levels are higher in synovial fluid than in plasma and in vitro cartilage explants release PPi into the extracellular medium. (Ryan, L. M. et al. (1996) J. Rheumatol. 23:214–219.)

Enzymes that hydrolyze nucleotide triphosphates and release PPi are called nucleotide pyrophosphohydrolases (NTPPH). NTPPH activity is found in synovial fluid and correlates with the production of PPi. Elevated ATP levels have been found in joint fluids of patients with CPPD deposition, and addition of extracellular ATP to joint tissues and fluids results in the production of PPi. (Park, W. I. et al. (1996) J. Rheumatol. 23:665–671.) The levels of molecules with NTPPH activity are higher in extracts from cartilage containing CPPD crystals than from cartilage lacking crystals. Matrix vesicles released from articular cartilage in vitro show high NTPPH activity and produce CPPD in the presence of calcium and ATP. (Derfus, B. A. et al. (1992) Arthritis. Rheum. 35:231–240.)

A protein demonstrating NTPPH activity and having a molecular weight of 61 kD was recently purified from porcine articular cartilage explant conditioned medium. (Masuda, I. et al. (1995) J. Clin. Invest. 95:699–704.) The first 26 residues of the amino-terminus were sequenced and showed no homology to any protein in public databases. Antipeptide antibodies were generated against the 61 kD porcine protein, and the antisera identified the original 61 kD protein and an additional 127 kD vesicle-associated protein in conditioned medium from cultures of both chondrocytes and cartilage explants. The 61 kD isoform is believed to be a catalytically active proteolytic fragment of the 127 kD protein. Both the 61 kD and the 127 kD isoforms were identified in human synovial fluids, and a 100 kD protein was identified in human serum. Using the antipeptide antibody on immunoblots of tissue extracts, NTPPH expression was found only in articular tissues, e.g., hyaline cartilage, fibrocartilage, tendon, and ligament, in which CPPD deposition occurs. (Cardenal, A. et al. (1996) Arthritis Rheum. 39:252–256; Cardenal, A. et al. (1996) Arthritis Rheum. 39:245–251.) Recently, a partial porcine NTPPH cDNA was isolated. (Masuda, I. et al. (1997) Gene 197:227–282.)

A full length human nucleotide pyrophosphohydrolase (NTPPH-1) has been cloned using a cDNA clone isolated from a cartilage cDNA library. Northern analysis of human, dog, and rabbit joint tissue RNA samples indicated elevated levels of NTPPH-1 expression in articular cartilage, and lower, but significant, levels of expression in synovium, meniscus, tendon and ligament. Expression studies on additional human tissues demonstrated significant mRNA levels in skeletal muscle, heart muscle, and bone marrow; and lower, but detectable, levels in trachea, spinal cord, thyroid, stomach, testis, uterus, small intestine, colon, thymus, placenta, lymph, and adrenal tissue.

The discovery of a new human nucleotide pyrophosphohydrolase, NTPPH-2, and the polynucleotides encoding it satisfies a need in the art by providing new compositions which are useful in the diagnosis, prevention and treatment of arthropathies, immunological disorders, and cancers.

SUMMARY OF THE INVENTION

The invention features a substantially purified polypeptide, human nucleotide pyrophosphohydrolase-2 (NTPPH-2), comprising the amino acid sequence of SEQ ID NO:1 or a fragment of SEQ ID NO:1.

The invention further provides a substantially purified variant of NTPPH-2 having at least 90% amino acid identity to the amino acid sequence of SEQ ID NO:1 or a fragment of SEQ ID NO:1. The invention also provides an isolated and purified polynucleotide encoding the polypeptide comprising the amino acid of SEQ ID NO:1 or a fragment of SEQ ID NO:1. The invention also includes an isolated and purified polynucleotide variant having at least 90% polynucleotide identity to the polynucleotide encoding the polypeptide comprising the amino acid sequence of SEQ ID NO:1 or a fragment of SEQ ID NO:1.

Additionally, the invention provides a composition comprising a polynucleotide encoding the polypeptide comprising the amino acid sequence of SEQ ID NO:1 or a fragment of SEQ ID NO:1. The invention further provides an isolated and purified polynucleotide which hybridizes under stringent conditions to the polynucleotide encoding the polypeptide comprising the amino acid sequence of SEQ ID NO:1 or a fragment of SEQ ID NO:1, as well as an isolated and purified polynucleotide which is complementary to the polynucleotide encoding the polypeptide comprising the amino acid sequence of SEQ ID NO:1 or a fragment of SEQ ID NO:1.

The invention also provides an isolated and purified polynucleotide comprising SEQ ID NO:2 or a fragment of SEQ ID NO:2, and an isolated and purified polynucleotide variant having at least 90% polynucleotide identity to the polynucleotide comprising SEQ ID NO:2 or a fragment of SEQ ID NO:2. The invention provides a useful fragment of SEQ ID NO:2 selected from the group consisting of nucleotides 55 through 75, 481 through 507, 646 through 669, 2182 through 4149, 1726 through 4149, 757 through 4149, and 113 through 4149 of SEQ ID NO:2. The invention additionally provides an isolated and purified polynucleotide which has been deposited as Accession No. 98615 in the American Type Culture Collection. The invention also provides an isolated and purified polynucleotide which is complementary to the polynucleotide comprising SEQ ID NO:2 or a fragment of SEQ ID NO:2.

The invention further provides an expression vector containing at least a fragment of the polynucleotide encoding the polypeptide comprising the amino acid sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide encoding NTPPH-2 under conditions suitable for the expression of the polypeptide; and (b) recovering the polypeptide from the host cell culture.

The invention also provides a pharmaceutical composition comprising a substantially purified NTPPH-2 having the amino acid sequence of SEQ ID NO:1 or a fragment of SEQ ID NO:1 and a suitable pharmaceutical carrier.

The invention further includes a purified antibody which binds to a polypeptide comprising the amino acid sequence of SEQ ID NO:1 or a fragment of SEQ ID NO:1, as well as a purified agonist and a purified antagonist of the polypeptide.

The invention also provides a method for detecting a polynucleotide encoding an NTPPH-2 having an amino acid sequence of SEQ ID NO:1 in a biological sample containing nucleic acids, the method comprising the steps of: (a) hybridizing the complement of the polynucleotide encoding the polypeptide comprising SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding NTPPH-2 in the biological sample. In one aspect, the nucleic acids of the biological sample are amplified by the polymerase chain reaction prior to the hybridizing step.

The invention also provides a method for treating or preventing an arthropathy, comprising administering to a subject in need of such treatment an effective amount of an antagonist of NTPPH-2.

The invention also provides a method for treating or preventing an immunological disorder comprising administering to a subject in need of such treatment an effective amount of an antagonist of NTPPH-2.

The invention also provides a method for treating or preventing a cancer comprising administering to a subject in need of such treatment an effective amount of an antagonist of NTPPH-2.

The invention also provides a method for detecting NTPPH-2 in a biological sample comprising the steps of: a) providing a biological sample; b) combining the biological sample and an antibody which binds to a polypeptide comprising the amino acid sequence of SEQ ID NO:1 or a fragment of SEQ ID NO:1 under suitable conditions for complex formation to occur between NTPPH-2 and the antibody; and c) detecting complex formation between NTPPH-2 and the antibody, thereby establishing the presence of NTPPH-2 in the biological sample.

The invention provides a method for screening a library of small molecules to identify a molecule which binds NTPPH-2, the method comprising the steps of: a) providing a library of small molecules; b) combining the library of small molecules with the polypeptide of SEQ ID NO:2 or a fragment of SEQ ID NO:2 under suitable conditions for complex formation; and c) detecting complex formation wherein the presence of the complex identifies a small molecule which binds NTPPH-2.

The invention also provides a method for identifying an agonist, the method comprising the steps of: a) delivering one of the small molecules identified by screening a library of small molecules and gamma labeled ATP into cells transformed with a vector expressing NTPPH-2; b) growing the cells under suitable conditions; and c) assaying for an increased amount of PPi thereby establishing that the small molecule is an agonist.

The invention further provides a method for identifying an antagonist, the method comprising the steps of: a) delivering one of the small molecules identified by screening a library of small molecules and gamma labeled ATP into cells transformed with a vector expressing NTPPH-2; b) growing the cells under suitable conditions; and c) assaying for a decreased amount of PPi thereby establishing that the small molecule is an antagonist.

BRIEF DESCRIPTION OF THE FIGURES

FIGS. 1A, 1B, 1C, 1D, 1E, 1F, 1G, 1H, 1I, 1J, and 1K show the amino acid sequence (1388013; SEQ ID NO:1) and nucleic acid sequence (SEQ ID NO:2) of human nucleotide pyrophosphohydrolase, NTPPH-2. The alignment was produced using MacDNAsis PRO™ software (Hitachi Software Engineering Co. Ltd. San Bruno, Calif.).

FIGS. 2A, 2B, and 2C show sequence alignments between NTPPH-2 (SEQ ID NO:1) and NTPPH-1 (422069; SEQ ID NO:3).

DESCRIPTION OF THE INVENTION

Figure 3A:
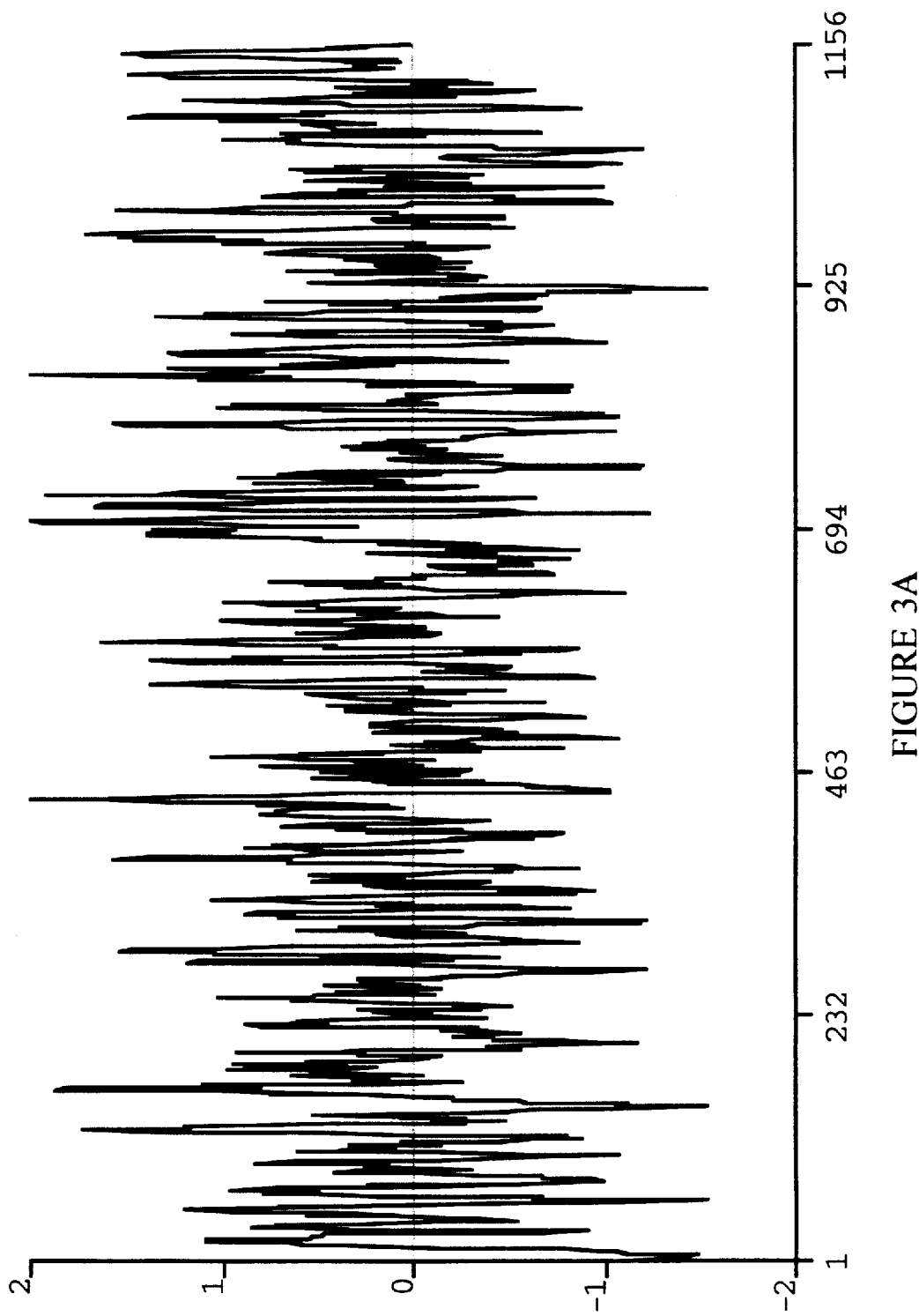
FIGS. 3A and 3B show hydrophobicity plots for NTPPH-2 (SEQ ID NO:1 ) and NTPPH-1 (SEQ ID NO:3); the positive X axis reflects amino acid position, and the negative Y axis, hydrophobicity (MacDNAsis PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, e.g., a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"NTPPH-2," as used herein, refers to the amino acid sequences of substantially purified NTPPH-2 obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to NTPPH-2, increases or prolongs the duration of the effect of NTPPH-2. Agonists may include proteins, nucleic acids, carbohydrates, or any other molecules which bind to and modulate the effect of NTPPH-2.

An "allele" or an "allelic sequence," as these terms are used herein, is an alternative form of the gene encoding NTPPH-2. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding NTPPH-2, as described herein, include those sequences with deletions, insertions, or substitutions of different nucleotides, resulting in a polynucleotide the same as NTPPH-2 or a polypeptide with at least one functional characteristic of NTPPH-2. Included within this definition are polymorphisms which may or may not be readily detectable using a particular oligonucleotide probe of the polynucleotide encoding NTPPH-2, and improper or unexpected hybridization to alleles, with a locus other than the normal chromosomal locus for the polynucleotide sequence encoding NTPPH-2. The encoded protein may also be "altered," and may contain deletions, insertions, or substitutions of amino acid residues which produce a silent change and result in a functionally equivalent NTPPH-2. Deliberate amino acid substitutions may be made on the basis of similarity in polarity, charge, solubility, hydrophobicity, hydrophilicity, and/or the amphipathic nature of the residues, as long as the biological or immunological activity of NTPPH-2 is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments" refers to fragments of NTPPH-2 which are preferably about 5 to about 15 amino acids in length and which retain some biological activity or immunological activity of NTPPH-2. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (Dieffenbach, C. W. and G. S. Dveksler (1995) *PCR Primer, a Laboratory Manual,* Cold Spring Harbor Press, Plainview, N.Y.)

The term "antagonist," as it is used herein, refers to a molecule which, when bound to NTPPH-2, decreases the amount or the duration of the effect of the biological or immunological activity of NTPPH-2. Antagonists may include proteins, nucleic acids, carbohydrates, antibodies, or any other molecules which decrease the effect of NTPPH-2.

As used herein, the term "antibody" refers to intact molecules as well as to fragments thereof, such as Fab, $F(ab')_2$, and Fv fragments, which are capable of binding the epitopic determinant. Antibodies that bind NTPPH-2 polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific DNA or RNA sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural. regulatory, or biochemical functions of a naturally occurring molecule. Likewise, "immunologically active" refers to the capability of the natural, recombinant, or synthetic NTPPH-2, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation or an aqueous solution. Compositions comprising polynucleotide sequences encoding NTPPH-2 or fragments of NTPPH-2 may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding NTPPH-2, by northern analysis is indicative of the presence of nucleic acids encoding NTPPH-2 in a sample, and thereby correlates with expression of the transcript from the polynucleotide encoding NTPPH-2.

A "deletion," as the term is used herein, refers to a change in the amino acid or nucleotide sequence that results in the absence of one or more amino acid residues or nucleotides.

The term "derivative," as used herein, refers to the chemical modification of NTPPH-2, of a polynucleotide sequence encoding NTPPH-2, or of a polynucleotide sequence complementary to a polynucleotide sequence encoding NTPPH-2. Chemical modifications of a polynucleotide sequence can include, e.g., replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

"Human artificial chromosomes" (HACs), as described herein, are linear microchromosomes which may contain DNA sequences of about 10 kb to 10 mb in size, and which contain all of the elements required for stable mitotic chromosome segregation and maintenance. (Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

"Inflammation" as used herein is interchangeable with "inmmune response", with both terms referring to a condition associated with trauma, immune disorders, and infectious or genetic diseases and are characterized by production of cytokines, chemokines, and other signaling molecules which activate cellular and systemic defense systems.

The words "insertion" or "addition," as used herein, refer to changes in an amino acid or nucleotide sequence resulting in the addition of one or more amino acid residues or nucleotides, respectively, to the sequence found in the naturally occurring molecule.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as it appears herein, refers to a change in the activity of NTPPH-2. For example, modulation may cause an increase or a decrease in protein activity, binding characteristics, or any other biological, functional, or immunological properties of NTPPH-2.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (Nielsen, P. E. et al. (1993) Anticancer Drug Des. 8:53–63.

The term "sample," as used herein, is used in its broadest sense. A biological sample suspected of containing nucleic acids encoding NTPPH-2, or fragments thereof, or NTPPH-2 itself may comprise a bodily fluid; an extract from a cell, chromosome, organelle, or membrane isolated from a cell; a cell; genomic DNA, RNA, or cDNA (in solution or bound to a solid support); a tissue; a tissue print; and the like.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, e.g., the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and refers to cells which transiently express the inserted DNA or RNA for limited periods of time.

A "variant" of NTPPH-2, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, e.g., DNASTAR software.

The Invention

The invention is based on the discovery of a new human nucleotide pyrophosphohydrolase (NTPPH-2), the polynucleotides encoding NTPPH-2, and the use of these compositions for the diagnosis, treatment, or prevention of arthropathies, immunological disorders, and cancers.

Nucleic acids encoding the NTPPH-2 of the present invention were identified in Incyte Clones 1388013, 1423393, and 1423402 from the osteoarthritic chondrocyte cDNA library (SATPF 1008) using a computer search for nucleotide sequence homology and the partial porcine cDNA sequence. (Masuda, supra.) A 4.1 kb sequence was identified in the chondrocyte library using the cDNA insert from Incyte Clone 1423393 as a hybridization probe. When a 700 bp restriction fragment from the 5' most coding region of the 4.1 kb clone was used to rescreen the osteoarthritic chondrocyte library, the full length gene encoding NTPPH-2 with appropriate Kozak initiation and signal sequence was obtained. This sequence does not match any sequence in the public DNA sequence database. The cDNA for full length NTPPH-2 of this application has been deposited as Accession No. 98615 at the American Type Culture Collection, Bethesda, Md. on Dec. 9, 1997.

Figure 3B:
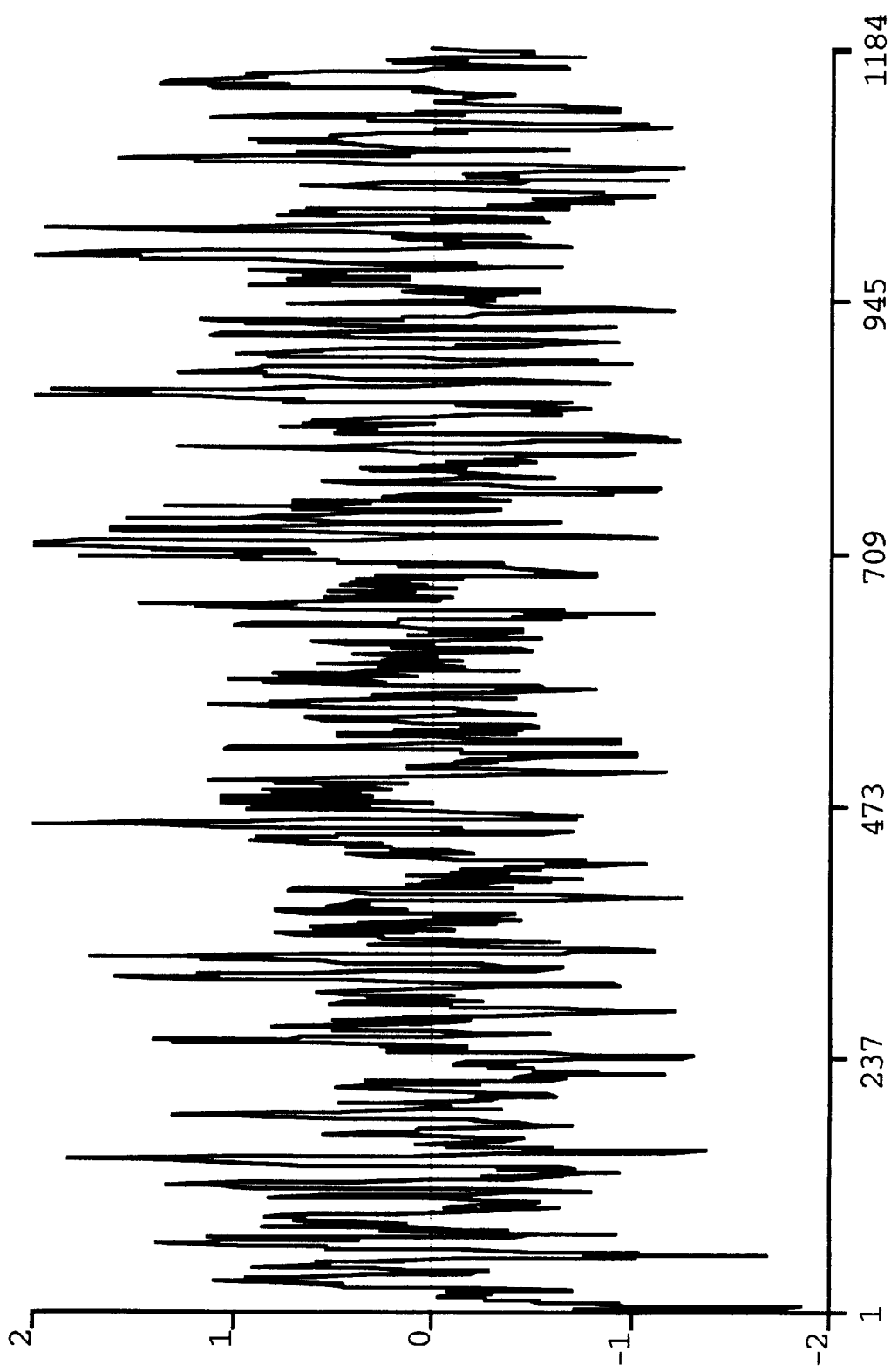

In one embodiment, the invention encompasses a polypeptide comprising the amino acid sequence of SEQ ID NO:1. NTPPH-2 is 1156 amino acids in length (FIGS. 1A–1K) and has three potential N-glycosylation sites at $N_{276}$, $N_{308}$, $N_{329}$, 25 potential phosphorylation sites at $T_{24}$, $S_{135}$, $S_{229}$, $T_{245}$, $S_{267}$, $S_{325}$, $T_{331}$, $T_{372}$, $S_{427}$, $S_{434}$, $S_{439}$, $T_{517}$, $T_{523}$, $Y_{599}$, $T_{608}$, $S_{630}$, $T_{750}$, $T_{847}$, $S_{883}$, $Y_{909}$, $S_{977}$, $S_{1017}$, $T_{1063}$, $S_{1068}$, and $T_{1149}$. As shown in FIGS. 2A, 2B, and 2C, NTPPH-2 has chemical and structural homology with NTPPH-1 (SEQ ID NO:3). In particular, NTPPH-2 and NTPPH-1 share 50% sequence identity. Fragments of the nucleic acid sequence of SEQ ID NO:2 useful for designing oligonucleotides or to be used directly as hybridization probes to distinguish between these homologous molecules include the fragments from nucleotides 55 through 75, 481 through 507, 646 through 669, 2182 through 4149, 1726 through 4149, 757 through 4149, and 113 through 4149. As illustrated by FIGS. 3A and 3B, NTPPH-2 and NTPPH-1 have similar hydrophobicity plots and both show a hydrophobic signal sequence. The predicted isoelectric points for NTPPH-2 and NTPPH-1 are 8.07 and 8.21, respectively. Membrane-based northern analysis showed the highest level of NTPPH-2 mRNA expression in cartilage and lower, but significant, expression in testes, trachea, and bone marrow. Electronic northern analysis shows the expression of this sequence in various libraries at least 57% of which involve immunological response and many of which are cartilage or joint related and at least 26% of which involve immortalized or cancerous cells and tissues. Of particular note is the expression of NTPPH-2 in rheumatoid and osteoarthritic synovial, chondrocyte, and tibial libraries.

The invention also encompasses NTPPH-2 variants. A preferred NTPPH-2 variant is one having at least about 80%, more preferably at least about 90%, and most preferably at least about 95% amino acid sequence identity to the NTPPH-2 amino acid sequence and which retains at least one biological, immunological or other functional characteristic or activity of NTPPH-2.

The invention also encompasses polynucleotides which encode NTPPH-2. In a particular embodiment, the invention encompasses a polynucleotide sequence comprising the sequence of SEQ ID NO:2, which encodes an NTPPH-2.

The invention also encompasses a variant of a polynucleotide sequence encoding NTPPH-2. In particular, such a variant polynucleotide sequence will have at least about 80%, more preferably at least about 90%, and most preferably at least about 95% polynucleotide sequence identity to the polynucleotide sequence encoding NTPPH-2. A particular aspect of the invention encompasses a variant of SEQ ID NO:2 which has at least about 80%, more preferably at least about 90%, and most preferably at least about 95% polynucleotide sequence identity to SEQ ID NO:2. In addition, the amino acid sequences encoded by these variants may have at least one functional or structural characteristic of NTPPH-2.

It will be appreciated by those skilled in the art that as a result of the degeneracy of the genetic code, a multitude of polynucleotide sequences encoding NTPPH-2, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring NTPPH-2, and all such variations are to be considered as being specifically disclosed.

Although nucleotide sequences which encode NTPPH-2 and its variants are preferably capable of hybridizing to the nucleotide sequence of the naturally occurring NTPPH-2 under appropriately selected conditions of stringency, it may be advantageous to produce nucleotide sequences encoding NTPPH-2 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding NTPPH-2 and its derivatives without altering the encoded amino acid sequences include the production of RNA transcripts having more desirable properties, such as a greater half-life, than transcripts produced from the naturally occurring sequence.

The invention also encompasses production of DNA sequences which encode NTPPH-2 and NTPPH-2 derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding NTPPH-2 or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–51 1.)

Methods for DNA sequencing are well known and generally available in the art and may be used to practice any of the embodiments of the invention. The methods may employ such enzymes as the Klenow fragment of DNA polymerase I, Sequenase® (U.S. Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by GIBCO/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding NTPPH-2 may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (Sarkar, G. (1993) PCR Methods Applic. 2:318–322.) In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (Triglia, T. et al. (1988) Nucleic Acids Res. 16:8186.) The primers may be designed using commercially available software such as OLIGO 4.06 Primer Analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Another method which may be used to retrieve unknown sequences is that of Parker, J. D. et al. (1991; Nucleic Acids Res. 19:3055–3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode NTPPH-2 may be used in recombinant DNA molecules to direct expression of NTPPH-2, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express NTPPH-2.

As will be understood by those of skill in the art, it may be advantageous to produce NTPPH-2-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter NTPPH-2 encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding NTPPH-2 may be ligated to a heterologous sequence to encode a fusion protein. For example, to screen peptide libraries for inhibitors of NTPPH-2 activity, it may be useful to encode a chimeric NTPPH-2 protein that can be recognized by a commercially available antibody. A fusion protein may also be engineered to contain a cleavage site located between the NTPPH-2 encoding sequence and the heterologous protein sequence, so that NTPPH-2 may be cleaved and purified away from the heterologous moiety.

In another embodiment, sequences encoding NTPPH-2 may be synthesized, in whole or in part, using chemical methods well known in the art (Caruthers, M. H. et al. (1980) Nucl. Acids Res. Symp. Ser. 215–223, and Horn, T. et al. (1980) Nucl. Acids Res. Symp. Ser. 225–232). Alternatively, the protein itself may be produced using chemical methods to synthesize the amino acid sequence of NTPPH-2, or a fragment thereof. For example, peptide synthesis can be performed using various solid-phase techniques (Roberge, J. Y. et al. (1995) Science 269:202–204) and automated synthesis may be achieved using the ABI 431A Peptide Synthesizer (Perkin Elmer).

The newly synthesized peptide may be substantially purified by preparative high performance liquid chromatography. (Creighton, T. (1983) *Proteins, Structures and Molecular Principles,* WH Freeman and Co., New York, N.Y.) The composition of the synthetic peptides may be confirmed by amino acid analysis or by sequencing. (the Edman degradation procedure described in Creighton, supra.) Additionally, the amino acid sequence of NTPPH-2, or any part thereof, may be altered during direct synthesis and/or combined with sequences from other proteins, or any part thereof, to produce a variant polypeptide.

In order to express a biologically active NTPPH-2, the nucleotide sequences encoding NTPPH-2 or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding NTPPH-2 and appropriate transcriptional and translational control elements. These methods include in vitro recombinant DNA techniques, synthetic techniques, and in vivo genetic recombination. Such techniques are described in Sambrook, J. et al. (1989; *Molecular Cloning, A Laboratory Manual,* Cold Spring Harbor Press, Plainview, N.Y.) and Ausubel, F. M. et al. (1989; *Current Protocols in Molecular Biology,* John Wiley & Sons, New York, N.Y.)

A variety of expression vector/host systems may be utilized to contain and express sequences encoding NTPPH-2. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, La Jolla, Calif.) or pSport1™ plasmid (GIBCO/BRL), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding NTPPH-2, vectors based on SV40 or EBV may be used with an appropriate selectable marker.

In bacterial systems, a number of expression vectors may be selected depending upon the use intended for NTPPH-2. For example, when large quantities of NTPPH-2 are needed for the induction of antibodies, vectors which direct high level expression of fusion proteins that are readily purified may be used. Such vectors include, but are not limited to, multifunctional *E. coli* cloning and expression vectors such as Bluescript® (Stratagene), in which the sequence encoding NTPPH-2 may be ligated into the vector in frame with sequences for the amino-terminal Met and the subsequent 7 residues of β-galactosidase so that a hybrid protein is produced, pIN vectors (Van Heeke, G. and S. M. Schuster (1989) J. Biol. Chem. 264:5503–5509), and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. For reviews, see Ausubel (supra) and Grant et al. (1987; Methods Enzymol. 153:516–544.)

In cases where plant expression vectors are used, the expression of sequences encoding NTPPH-2 may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews (Hobbs, S. or Murry, L. E. in *McGraw Hill Yearbook of Science and Technology* (1992) McGraw Hill, New York, N.Y., pp. 191–196).

An insect system may also be used to express NTPPH-2. For example, in one such system, *Autographa californica* nuclear polyhedrosis virus (AcNPV) is used as a vector to express foreign genes in *Spodoptera frugiperda* cells or in Trichoplusia larvae. The sequences encoding NTPPH-2 may be cloned into a non-essential region of the virus, such as the polyhedrin gene, and placed under control of the polyhedrin promoter. Successful insertion of NTPPH-2 will render the polyhedrin gene inactive and produce recombinant virus lacking coat protein. The recombinant viruses may then be used to infect, e.g., *S. frugiperda* cells or Trichoplusia larvae in which NTPPH-2 may be expressed. (Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding NTPPH-2 may be ligated into an adenovirus transcription/translation complex consisting of the late promoter and tripartite leader sequence. Insertion in a non-essential E1 or E3 region of the viral genome may be used to obtain a viable virus which is capable of expressing NTPPH-2 in infected host cells. (Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 mb are constructed and delivered via conventional delivery methods (liposomes, polycationic amino polymers, or vesicles) for therapeutic purposes.

Specific initiation signals may also be used to achieve more efficient translation of sequences encoding NTPPH-2. Such signals include the ATG initiation codon and adjacent sequences. In cases where sequences encoding NTPPH-2 and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used, such as those described in the literature. (Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing NTPPH-2 can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes (Wigler, M. et al. (1977) Cell 11:223–32) and adenine phosphoribosyltransferase genes (Lowy, I. et al. (1980) Cell 22:817–23), which can be employed in tk or apr cells, respectively. Also, antimetabolite, antibiotic, or herbicide resistance can be used as the basis for selection. For example, dhfr confers resistance to methotrexate (Wigler, M. et al. (1980) Proc. Natl. Acad. Sci. 77:3567–70); npt confers resistance to the aminoglycosides neomycin and G-418 (Colbere-Garapin, F. et al. (1981) J. Mol. Biol. 150:1–14); and als or pat confer resistance to chlorsulfuron and phosphinotricin acetyltransferase, respectively. (Murry, supra.) Additional selectable genes have been described, e.g., trpB, which allows cells to utilize indole in place of tryptophan, or hisD, which allows cells to utilize histinol in place of histidine. (Hartman, S. C. and R. C. Mulligan (1988) Proc. Natl. Acad. Sci. 85:8047–51.) Recently, the use of visible markers has gained popularity with such markers as anthocyanins, β glucuronidase and its substrate GUS, and luciferase and its substrate luciferin. These markers can be used not only to identify transformants, but also to quantify the amount of transient or stable protein expression attributable to a specific vector system. (Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding NTPPH-2 is inserted within a marker gene sequence, transformed cells containing sequences encoding NTPPH-2 can be identified by the absence of marker gene function. Alternatively, a marker gene can be placed in tandem with a sequence encoding NTPPH-2 under the control of a single promoter. Expression of the marker gene in response to induction or selection usually indicates expression of the tandem gene as well.

Alternatively, host cells which contain the nucleic acid sequence encoding NTPPH-2 and express NTPPH-2 may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding NTPPH-2 can be detected by DNA-DNA or DNA-RNA hybridization or amplification using probes or fragments or fragments of polynucleotides encoding NTPPH-2. Nucleic acid amplification based assays involve the use of oligonucleotides or oligomers based on the sequences encoding NTPPH-2 to detect transformants containing DNA or RNA encoding NTPPH-2.

A variety of protocols for detecting and measuring the expression of NTPPH-2, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on NTPPH-2 is preferred, but a competitive binding assay may be employed. These and other assays are well described in the art, e.g., in Hampton, R. et al. (1990; *Serological Methods, a Laboratory Manual,* APS Press, St Paul, Minn.) and in Maddox, D. E. et al. (1983; J. Exp. Med. 158:1211–1216.)

A wide variety of labels and conjugation techniques are known by those skilled in the art and may be used in various nucleic acid and amino acid assays. Means for producing labeled hybridization or PCR probes for detecting sequences related to polynucleotides encoding NTPPH-2 include oligolabeling, nick translation, end-labeling, or PCR amplification using a labeled nucleotide. Alternatively, the sequences encoding NTPPH-2, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding NTPPH-2 may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode NTPPH-2 may be designed to contain signal sequences which direct secretion of NTPPH-2 through a prokaryotic or eukaryotic cell membrane. Other constructions may be used to join sequences encoding NTPPH-2 to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences, such as those specific for Factor XA or enterokinase (Invitrogen, San Diego, Calif.), between the purification domain and the NTPPH-2 encoding sequence may be used to facilitate purification. One such expression vector provides for expression of a fusion protein containing NTPPH-2 and a nucleic acid encoding 6 histidine residues preceding a thioredoxin or an enterokinase cleavage site. The histidine residues facilitate purification by immobilized metal ion affinity chromatography (IMIAC; described in Porath, J. et al. (1992) Prot. Exp. Purif 3: 263–28 1), while the enterokinase cleavage site provides a means for purifying NTPPH-2 from the fusion protein. A discussion of vectors which contain fusion proteins is provided in Kroll, D. J. et al. (1993; DNA Cell Biol. 12:441–453.)

Fragments of NTPPH-2 may be produced not only by recombinant production, but also by direct peptide synthesis using solid-phase techniques. (Merrifield J. (1963) J. Am. Chem. Soc. 85:2149–2154.) Protein synthesis may be performed by manual techniques or by automation. Automated synthesis may be achieved, e.g., using the Applied Biosystems 431A Peptide Synthesizer (Perkin Elmer). Various fragments of NTPPH-2 may be synthesized separately and the n combined to produce the full length molecule.

Therapeutics

Chemical and structural homology exists between NTPPH-2 and human NTPPH-1 (SEQ ID NO:3). Transcripts hybridizing to the NTPPH-2 cDNA we re detected in cartilage, testes, trachea, and bone marrow tissues. Electronic northern analysis showed expression of NTPPH-2 in tissues with an immunological association (57%; including synovial and cartilage tissues), and in cancerous tissues (26%). Therefore, NTPPH-2 appears to play a role in arthropathies, immunological disorders, and cancers.

Therefore, in one embodiment, an antagonist of NTPPH-2 may be administered to a subject to prevent or treat an arthropathy. Arthropathies include, but are not limited to, Behcet's syndrome, Charcot osteoarthropathy, CPPD disease, diabetic neuropathic arthropathy, degenerative joint dis ease, fibromyalgias, hemachromatosis, hemophilic arthropathy, Jaccoud's type arthropathy, lupus erythematosus, mixed connective tissue disease, Muckle-Wells syndrome, osteoarthritis, progressive systemic sclerosis, pseudogout, psoriasis, Reiter's syndrome, rheumatoid arthritis, Sjögren's syndrome, and spondyloarthropathies. In one aspect, an antibody which specifically binds NTPPH-2 may be used directly as an antagonist or indirectly as a targeting or delivery mechanism for bringing a pharmaceutical agent to cells or tissue which express NTPPH-2.

In another embodiment, a vector expressing the complement of the polynucleotide encoding NTPPH-2 may be administered to a subject to treat or prevent an arthropathy including, but not limited to, those described above.

In another embodiment, an antagonist of NTPPH-2 may be administered to a subject to prevent or treat an immunological disorder. Immunological disorders include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, multiple sclerosis, myasthenia gravis, myocardial or pericardial inflammation, osteoporosis, pancreatitis, polymyositis, scieroderma, autoimmune thyroiditis and ulcerative colitis; complications of cancer, hemodialysis, and extracorporeal circulation; viral, bacterial, fungal, parasitic, protozoal, and helminthic infections; and trauma. Such disorders may be characterized by the production of cytokines and the multiplication of leukocytes, macrophages, and other cells which may cause tissue damage or the inappropriate proliferation of tissues in response to inflammatory mediators or the generation of granulomatous tissues. In one aspect, an antibody which specifically binds NTPPH-2 may be used directly as an antagonist or indirectly as a targeting or delivery mechanism for bringing a pharmaceutical agent to cells or tissue which express NTPPH-2.

In another embodiment, a vector expressing the complement of the polynucleotide encoding NTPPH-2 may be administered to a subject to treat or prevent an immunological disorder including, but not limited to, those described above.

In another embodiment, an antagonist of NTPPH-2 may be administered to a subject to prevent or treat a cancer. Cancers include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cartilage, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds NTPPH-2 may be used directly as an antagonist or indirectly as a targeting or delivery mechanism for bringing a pharmaceutical agent to cells or tissue which express NTPPH-2.

In another embodiment, a vector expressing the complement of the polynucleotide encoding NTPPH-2 may be administered to a subject to treat or prevent a cancer including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of NTPPH-2 may be produced using methods which are generally known in the art. In particular, purified NTPPH-2 may be used to produce antibodies or to screen libraries of pharmaceutical agents to identify those which specifically bind NTPPH-2. Antibodies to NTPPH-2 may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with NTPPH-2 or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

For the production of antibodies, binding proteins, or peptides which bind specifically to NTPPH-2, libraries of single chain antibodies, Fab fragments, other antibody fragments, non-antibody protein domains, or peptides may be screened. The libraries could be generated using phage display, other recombinant DNA methods, or peptide synthesis (Vaughan, T. J. et al.(1996) Nature Biotechnology 14:309–314). The libraries would be screened using methods which are well known in the art to identify sequences which demonstrate specific binding to NTPPH-2.

It is preferred that the oligopeptides, peptides, or fragments used to induce antibodies to NTPPH-2 have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of NTPPH-2 amino acids may be fused with those of another protein, such as KLH, and antibodies to the chimeric molecule may be produced.

Monoclonal antibodies to NTPPH-2 may be prepared using any technique which provides for the production of antibody molecules by continuous cell lines in culture. These include, but are not limited to, the hybridoma technique, the human B-cell hybridoma technique, and the EBV-hybridoma technique. (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce NTPPH-2-specific single chain antibodies. Antibodies with related specificity, but of distinct idiotypic composition, may be generated by chain shuffling from random combinatorial immunoglobulin libraries. (Burton D. R. (1991) Proc. Natl. Acad. Sci. 88:11120–11123.)

Antibodies may also be produced by inducing in vivo production in the lymphocyte population or by screening immunoglobulin libraries or panels of highly specific binding reagents as disclosed in the literature. (Orlandi, R. et al. (1989) Proc. Natl. Acad. Sci. 86: 3833–3837, and Winter, G. et al. (1991) Nature 349:293–299.)

Antibody fragments which contain specific binding sites for NTPPH-2 may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (Huse, W. D. et al. (1989) Science 254:1275–1281.)

Various immunoassays may be used to identify antibodies having the desired specificity. Numerous protocols for competitive binding or immunoradiometric assays using either polyclonal or monoclonal antibodies with established specificities are well known in the art. Such immunoassays typically involve the measurement of complex formation between NTPPH-2 and its specific antibody. A two-site, monoclonal-based immunoassay utilizing monoclonal antibodies reactive to two non-interfering NTPPH-2 epitopes is preferred, but a competitive binding assay may also be employed. (Maddox, supra.)

In another embodiment of the invention, the polynucleotides encoding NTPPH-2, or any fragment or complement thereof, may be used for therapeutic purposes. In one aspect, the complement of the polynucleotide encoding NTPPH-2 may be used in situations in which it would be desirable to block the transcription of the mRNA. In particular, cells may be transformed with sequences complementary to polynucleotides encoding NTPPH-2. Thus, complementary molecules or fragments may be used to modulate NTPPH-2 activity, or to achieve regulation of gene function. Such technology is now well known in the art, and sense or antisense oligonucleotides or larger fragments can be designed from various locations along the coding or control regions of sequences encoding NTPPH-2.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding NTPPH-2. These techniques are described, e.g., in Sambrook (supra) and in Ausubel (supra).

Genes encoding NTPPH-2 can be turned off by transforming a cell or tissue with expression vectors which express high levels of a polynucleotide or fragment thereof encoding NTPPH-2. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding NTPPH-2. Oligonucleotides derived from the transcription initiation site, e.g., between about positions –10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (Gee, J. E. et al. (1994) in Huber, B. E. and B. I. Carr, *Molecular and Immunologic Approaches*, Futura Publishing Co., Mt. Kisco, N.Y.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules specifically and efficiently catalyze endonucleolytic cleavage of sequences encoding NTPPH-2.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding NTPPH-2. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art, such as those described in Goldman, C. K. et al. (1997; Nature Biotechnology 15:462–466.)

Any of the therapeutic methods described above may be applied to any subject in need of such therapy, including, e.g., mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of NTPPH-2, antibodies to NTPPH-2, and mimetics, agonists, antagonists, or inhibitors of NTPPH-2. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences.* (Maack Publishing Co., Easton, Pa.)

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of NTPPH-2, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays of neoplastic cells, e.g., or in animal models, usually mice, rabbits, dogs, or pigs. An animal model may also be used to determine the appropriate concentration range and route of administration. Such information can then be used to determine useful doses and routes for administration in humans.

A therapeutically effective dose refers to that amount of active ingredient, e.g. NTPPH-2 or fragments thereof, antibodies of NTPPH-2, and agonists, antagonists or inhibitors of NTPPH-2, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, and it can be expressed as the LD50/ED50 ratio. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on the half-life and clearance rate of the particular formulation.

Normal dosage amounts may vary from 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind NTPPH-2 may be used for the diagnosis of disorders characterized by expression of NTPPH-2, or in assays to monitor patients being treated with NTPPH-2 or agonists, antagonists, and inhibitors of NTPPH-2. Antibodies useful for diagnostic purposes may be prepared in the same manner as those described above for therapeutics. Diagnostic assays for NTPPH-2 include methods which utilize the antibody and a label to detect NTPPH-2 in human body fluids or in extracts of cells or tissues The antibodies may be used with or without modification, and may be labeled by covalent or non-covalent joining with a reporter molecule. A wide variety of reporter molecules, several of which are described above, are known in the art and may be used.

A variety of protocols for measuring NTPPH-2, including ELISAs, RIAs, and FACS, are known in the art and provide a basis for diagnosing altered or abnormal levels of NTPPH-2 expression. Normal or standard values for NTPPH-2 expression are established by combining body fluids or cell extracts taken from normal mammalian subjects, preferably human, with antibody to NTPPH-2 under conditions suitable for complex formation. The method for detecting NTPPH-2 in a biological sample would comprise the steps of: a) providing a biological sample; b) combining the biological sample and an anti-NTPPH-2 antibody under conditions which are suitable for complex formation to occur between NTPPH-2 and the antibody; and c) detecting complex formation between NTPPH-2 and the antibody, thereby establishing the presence of NTPPH-2 in the biological sample. The amount of complex formation then may be quantified by various methods, preferably by photometric means. Quantities of NTPPH-2 expressed in subject, control, and disease samples from biopsied tissues are compared with the standard values. Deviation between standard and subject values establishes the parameters for diagnosing disease.

In another embodiment of the invention, the polynucleotides encoding NTPPH-2 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of NTPPH-2 may be correlated with disease. The diagnostic assay may be used to distinguish between absence, presence, and excess expression of NTPPH-2, and to monitor regulation of NTPPH-2 levels during therapeutic intervention.

In one aspect, hybridization with PCR probes which are capable of detecting polynucleotide sequences, including genomic sequences, encoding NTPPH-2 or closely related molecules may be used to identify nucleic acid sequences which encode NTPPH-2. The specificity of the probe, whether it is made from a highly specific region (e.g., the 5' regulatory region) or from a less specific region (e.g., the 3' coding region), and the stringency of the hybridization or amplification (maximal, high, intermediate, or low), will determine whether the probe identifies only naturally occurring sequences encoding NTPPH-2, alleles, or related sequences.

Probes may also be used for the detection of related sequences, and should preferably contain at least 50% of the nucleotides from any of the NTPPH-2 encoding sequences. The hybridization probes of the subject invention may be DNA or RNA and may be derived from the sequence of SEQ ID NO:2 or from genomic sequences including promoter and enhancer elements and introns of the naturally occurring NTPPH-2.

Means for producing specific hybridization probes for DNAs encoding NTPPH-2 include the cloning of polynucleotide sequences encoding NTPPH-2 or NTPPH-2 derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, e.g., by radionuclides such as $^{32}$P or $^{35}$S, or by enzymatic labels, such as alkaline phosphatase coupled to the probe via avidin/biotin coupling systems, and the like.

Polynucleotide sequences encoding NTPPH-2 may be used for the diagnosis of conditions or disorders which are associated with expression of NTPPH-2. Examples of such conditions or disorders include, but are not limited to, arthropathies, e.g., Behcet's syndrome, Charcot osteoarthropathy, CPPD disease, diabetic neuropathic arthropathy, degenerative joint disease, fibromyalgias, hemachromatosis, hemophilic arthropathy, Jaccoud's type arthropathy, lupus erythematosus, mixed connective tissue disease, Muckle-Wells syndrome, osteoarthritis, progressive systemic sclerosis, pseudogout, psoriasis, Reiter's syndrome, rheumatoid arthritis, Sjögren's syndrome, and spondyloarthropathies; immunological disorders, e.g., AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, multiple sclerosis, myasthenia gravis, myocardial or pericardial inflammation, osteoporosis, pancreatitis, polymyositis, scleroderma, and autoimmune thyroiditis; complications of cancer, hemodialysis, and extracorporeal circulation; viral, bacterial, fungal, parasitic, protozoal, and heiminthic infections; and trauma; and cancers, e.g., adenocarcinoma, leukemia, lymphoma, melanoma, myeloma, sarcoma, teratocarcinoma, and particularly cancers of the adrenal gland, bladder, bone, bone marrow, brain, breast, cartilage, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

The polynucleotide sequences encoding NTPPH-2 may be used in Southern or northern analysis, dot blot, or other membrane-based technologies; in PCR technologies; in dipstick, pin, and ELISA assays; and in microarrays utilizing fluids or tissues from patient biopsies to detect altered NTPPH-2 expression. Such qualitative or quantitative methods are well known in the art.

In a particular aspect, the nucleotide sequences encoding NTPPH-2 may be useful in assays that detect the presence of associated disorders, particularly those mentioned above. The nucleotide sequences encoding NTPPH-2 may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding NTPPH-2 in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of a disorder associated with expression of NTPPH-2, a normal or standard profile for expression is established. This may be accomplished by combining body fluids or cell extracts taken from normal subjects, either animal or human, with a sequence, or a fragment thereof, encoding NTPPH-2, under conditions suitable for hybridization or amplification. Standard hybridization may be quantified by comparing the values obtained from normal subjects with values from an experiment in which a known amount of a substantially purified polynucleotide is used. Standard-values obtained from normal samples may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to evaluate whether the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding NTPPH-2 may involve the use of PCR. Such oligomers may be chemically synthesized, generated enzymatically, or produced in vitro. Oligomers will preferably consist of two nucleotide sequences, one with sense orientation (5' to 3') and another with antisense orientation (3' to 5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of NTPPH-2 include radiolabeling or biotinylating nucleotides, coamplification of a control nucleic acid, and interpolating results from standard curves. (Melby, P. C. et al. (1993) J. Immunol. Methods 159:235–244, and Duplaa, C. et al. (1993) Anal. Biochem. 212:239–226.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image) and to identify genetic variants, mutations, and polymorphisms. This information may be used in determining gene function, in understanding the genetic basis of a disorder, in diagnosing a disorder, and in developing and monitoring the activities of therapeutic agents.

In one embodiment, the microarray is prepared and used according to methods known in the art, such as those described in published PCT application WO95/11995 (Chee et al.), Lockhart, D. J. et al. (1996; Nat. Biotech. 14:1675–1680), and Schena, M. et al. (1996; Proc. Natl. Acad. Sci. 93:10614–10619.)

The microarray is preferably composed of a large number of unique single-stranded nucleic acid sequences, usually either synthetic antisense oligonucleotides or fragments of cDNAs, fixed to a solid support. The oligonucleotides are preferably about 6 to 60 nucleotides in length, more preferably about 15 to 30 nucleotides in length, and most preferably about 20 to 25 nucleotides in length. For a certain type of microarray, it may be preferable to use oligonucleotides which are about 7 to 10 nucleotides in length. The microarray may contain oligonucleotides which cover the known 5' or 3' sequence, or may contain sequential oligonucleotides which cover the full length sequence or unique oligonucleotides selected from particular areas along the length of the sequence. Polynucleotides used in the microarray may be oligonucleotides specific to a gene or genes of interest in which at least a fragment of the sequence is known or oligonucleotides specific to one or more unidentified cDNAs common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from about 2 to 1,000,000.

In order to produce oligonucleotides to a known sequence for a microarray, the gene of interest is examined using a computer algorithm which starts at the 5' end, or, more preferably, at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon, any other type of membrane, filter, chip, glass slide, or any other suitable solid support.

In one aspect, the oligonucleotides may be synthesized on the surface of the substrate by using a chemical coupling procedure and an ink jet application apparatus, such as that described in published PCT application WO95/251116 (Baldeschweiler et al.). In another aspect, a grid array analogous to a dot or slot blot (HYBRIDOT® apparatus, GIBCO/BRL) may be used to arrange and link cDNA fragments or oligonucleotides to the surface of a substrate using a vacuum system or thermal, UV, mechanical or chemical bonding procedures. In yet another aspect, an array may be produced by hand or by using available devices, materials, and machines (including Brinkmann® multichannel pipettors or robotic instruments), and may contain 8, 24, 96, 384, 1536, or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and Oligolabeling or TransProbe kits (Pharmacia & Upjohn) well known in the area of hybridization technology.

Incubation conditions are adjusted so that hybridization occurs with precise complementarity or with varying degrees of complementarity between hybridizing sequences. After removal of nonhybridized probes, a scanner is used to determine the levels and patterns of fluorescence. The scanned images are examined to determine the degree of complementarity and the relative abundance of each oligonucleotide sequence on the microarray. A detection system may be used to measure the absence, presence, and amount of hybridization for all of the distinct sequences simultaneously. This data may be used for large scale correlation studies or for functional analysis of the sequences, mutations, variants, or polymorphisms among samples. (Heller, R. A. et al. (1997) Proc. Natl. Acad. Sci. 94:2150–2155.)

In another embodiment of the invention, nucleic acid sequences encoding NTPPH-2 may be used to generate hybridization probes useful for mapping the naturally occurring genomic sequence. The sequences may be mapped to a particular chromosome, to a specific region of a chromosome, or to artificial chromosome constructions, such as human artificial chromosomes (HACs), yeast artificial chromosomes (YACs), bacterial artificial chromosomes (BACs), bacterial P1 constructions, or single chromosome cDNA libraries, such as those reviewed in Price, C. M. (1993; Blood Rev. 7:127–134) and Trask, B. J. (1991; Trends Genet. 7:149–154.)

Fluorescent in situ hybridization (FISH, as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in various scientific journals or at the Online Mendelian Inheritance in Man (OMIM) site. Correlation between the location of the gene encoding NTPPH-2 on a physical chromosomal map and a specific disorder, or predisposition to a specific disorder, may help define the region of DNA associated with that disorder. The nucleotide sequences of the subject invention may be used to detect differences in gene sequences between normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, e.g., AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

In another embodiment of the invention, NTPPH-2, its catalytic or immunogenic fragments, or oligopeptides thereof can be used for screening libraries of compounds such as agonists or antagonists in any of a variety of drug screening techniques. The fragment employed in such screening may be free in solution, affixed to a solid support, borne on a cell surface, or located intracellularly. The formation of binding complexes between NTPPH-2 and the agent being tested may be measured.

The method provided for screening a library of small molecules to identify a molecule which binds NTPPH-2 comprises: a) providing a library of small molecules; b) combining the library of small molecules with the polypeptide of SEQ ID NO:2 or a fragment of SEQ ID NO:2 under conditions which are suitable for complex formation; and c) detecting complex formation wherein the presence of the complex identifies a small molecule which binds NTPPH-2. The method for identifying one of these small molecules which binds NTPPH-2 as an agonist comprises delivering a small molecule which binds NTPPH-2 and gamma labeled ATP into cells transformed with a vector expressing NTPPH-2, growing the cells under suitable conditions, and assaying for PPi. An increased amount of PPi establishes that the small molecule is an agonist which increases NTPPH-2 activity. The method for identifying an antagonist comprises delivering a small molecule which binds NTPPH-2 and gamma labeled ATP into cells transformed with a vector expressing NTPPH-2, growing the cells under suitable conditions, and assaying the media for PPi. A reduced amount of PPi establishes that the small molecule is an antagonist which reduces NTPPH-2 activity.

Another technique for drug screening which may be used provides for high throughput screening of compounds having suitable binding affinity to the protein of interest as described in published PCT application WO84/03564. In this method, large numbers of different small lest compounds are synthesized on a solid substrate, such as plastic pins or some other surface. The test compounds are reacted with NTPPH-2, or fragments thereof, and washed. Bound NTPPH-2 is then detected by methods well known in the art. Purified NTPPH-2 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding NTPPH-2 specifically compete with a test compound for binding NTPPH-2. In this manner, antibodies can be used to detect the presence of any peptide which shares one or more antigenic determinants with NTPPH-2.

In additional embodiments, the nucleotide sequences which encode NTPPH-2 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I SATPF 1008 cDNA Library Construction

The SATPF 1008 cDNA library was made from cartilage tissue obtained from four donors with end stage osteoarthritis. The osteoarthritic patients had received steroids such as prednisone and a variety of non-steroidal anti-inflammatory drugs. There was no stimulation with IL-1 (Pfizer Inc., Groton, Conn.).

The osteoarthritic cartilage tissue was harvested at joint replacement surgery and placed in Dulbecco's Modified Eagle Medium (D-MEM; Gibco/BRL) supplemented with antibiotics (penicillin, streptomycin, and gentamicin) and transported to Pfizer laboratories. The cartilage was removed aseptically from the underlying bone, rinsed in D-MEM and diced into small pieces (~4 $mm^2$), and placed in 100 mm petri dishes containing 20 ml of Neuman and Tytell's serum free medium (Gibco/BRL). Using the protocol of Mitchell et al. (1996) J. Clin. Invest. 97:761–768, the cartilage from each patient was digested with 4 mg/ml pronase (Sigma, St Louis, Mo.) for 1.5 hours, then subsequently digested with 3 mg/ml bacterial collagenase (Sigma) for 1.5 hours. The digested cartilage was filtered through a cell strainer to remove undigested material, and the cells were pelleted by centrifugation. The cell pellet was washed once with phosphate buffered saline (PBS) and then dissolved in 5 ml of buffer consisting of 5 M guanidine isothiocyanate, 10 mM EDTA, 50 mM Tris (pH 7.5) and 8% β mercaptoethanol. A five-fold volume of 4M LiCl was added to the buffer, and the mixture was stored in the refrigerator overnight. After centrifugation, the precipitate was washed once with 3 M LiCl and recentrifuged. The second precipitate was dissolved in a solution consisting of 0.1 % sodium dodecyl sulfate, 1 mM EDTA and 10 mM Tris (pH 7.5). The suspension was frozen at −70 C. and then vortexed during thawing (Cathala et al (1983; DNA 2:329–335).

Total RNA was extracted twice with phenol chloroform, once with chloroform, and then, precipitated with ethanol. Equal amounts of RNA from the four donors were combined and ethanol precipitated, resulting in 112 μg pooled RNA. Following centrifugation, the RNA pellet was redissolved in DEPC-treated, distilled, deionized water (DEPC-dd$H_2$O) and run over a CsCl gradient. The RNA was extracted with acid phenol (1×at pH 4.0, catalog #972Z, Ambion, Austin, Tex.), precipitated with ethanol and resuspended in DEPC-dd$H_2$O. The RNA was treated with RNase-free Dnase (Epicentre Technologies, Madison, Wis.) for 15 minutes, extracted with chloroform, precipitated and washed with ethanol, and dissolved in DEPC-dd$H_2$O.

The mRNA was handled according to the recommended protocols in the SuperScript Plasmid System for cDNA synthesis and plasmid cloning (Cat. #18248-013, Gibco/BRL). The cDNAs were fractionated on a Sepharose CL4B column (Cat. #275105-01; Pharmacia), and those cDNAs exceeding 400 bp were ligated into pINCY 1 (Incyte). The plasmid pINCY 1 was subsequently transformed into DH5α™ competent cells (Cat. #18258-012; Gibco/BRL).

II Isolation and Sequencing of cDNA Clones

Plasmid DNA was released from the cells and purified using the REAL Prep 96 plasmid kit (Catalog #26173, QIAGEN, Inc., Chatsworth, Calif.). The recommended protocol was employed except for the following changes: 1) the bacteria were cultured in 1 ml of sterile Terrific Broth (Catalog #22711, GIBCO/BRL ) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger, et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992; Protein Engineering 5:35–51), could have been used when dealing with primary sequence patterns and secondary structure gap penalties. The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV Cloning of Full Length NTPPH-2

A 2.3 kb cDNA sequence which encodes a partial porcine NTPPH (L. M. Ryan, Medical College of Wisconsin, Milwaukee, Wis.) was searched against NCBI public EST and in-house databases. Homologous sequences were found in the osteoarthritic cartilage libraries.

A 4.1 kb sequence was identified in using the chondrocyte library and the cDNA insert from Incyte Clone 1423393 as a hybridization probe. When a 700 bp restriction fragment from the 5' most coding region of the 4.1 kb clone was used to rescreen the osteoarthritic cartilage library, the full length cDNA encoding NTPPH-2 was identified. The full length cDNA was sequenced and found to contain an appropriate Kozak initiation and signal sequence. The cloned polynucleotide sequence was deposited with The American Type Culture Collection as Accession No. 98615 on Dec. 9, 1997.

V Northern Analysis

Human multiple tissue northern blots were obtained from Clontech (Palo Alto, Calif.). Human cartilage was treated with +/− human recombinant IL-1∞. For RNA preparation, chondrocytes were isolated via sequential digestion for 1.5 hours with pronase (4 mg/ml) followed by bacterial collagenase (3 mg/ml) for 3–5 hours. The chondrocytes were pelleted, and the cells lysed in guanidinium isothiocyanate. RNA was precipitated with LiCl as described in Mitchell et al. (supra.) Northern blot analysis was carried out using DNA probes labeled with a random primer kit (Pharmacia Biotech Inc. Piscataway, N.J.). The blots were hybridized overnight at 42° C. essentially as described in Sambrook et al. (supra); then washed three times in 3×SSC/0.1%SDS at room temperature and once in 0.3×SSC/0.1% SDS at 60° C. for 15 minutes.

Membrane-based northern analyses of human, dog and rabbit joint tissue RNA samples demonstrated the highest levels of NTPPH-2 mRNA expression in cartilage and lower, but significant, expression levels in testes, trachea, and bone marrow.

Computer techniques analogous to northern analysis were also performed using BLAST. (Altschul (1993) supra, Altschul (1990) supra.) The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

Electronic northern analysis shows the expression of this sequence in various libraries at least 57% of which involve immunological response and at least 26% of which are immortalized or cancerous. Of particular note is the expression of NTPPH-2 in rheumatoid and osteoarthritic synovial, chondrocyte, and tibial libraries.

VI Extension of NTPPH-2 Encoding Polynucleotides

The nucleic acid sequence encoding NTPPH-2 was used to design oligonucleotide primers for obtaining 5' regulatory sequences using an appropriate genomic library. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (GIBCO/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M.J. Research, Watertown, Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |

-continued

| | |
|---|---|
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra.) After incubation for one hour at 37° C., the E. coli mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, cornmercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

VII Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 μCi of [γ-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VIII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995).

In the alternative, a chemical coupling procedure and an ink jet device are used to synthesize oligomers on the surface of a substrate (Baldeschweiler, J. D. et al., PCT/WO95/25116). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

IX Complementary Polynucleotides

Sequence complementary to the NTPPH-2-encoding sequence, or any part thereof, is used to decrease or inhibit expression of naturally occurring NTPPH-2. Although use of oligonucleotides comprising from about 15 to about 30 base-pairs is described, essentially the same procedure is used with smaller or larger sequence fragments. Appropriate oligonucleotides are designed using Oligo 4.06 software and the sequence encoding NTPPH2. To inhibit transcription, a complementary oligonucleotide is designed from the most unique 5'sequence and used to prevent promoter binding to the coding sequence. To inhibit translation, a complementary oligonucleotide is designed to prevent ribosomal binding to the NTPPH-2-encoding transcript.

X Expression of NTPPH-2

The cDNA encoding NTPPH-2 is used to express both full-length and truncated forms of recombinant NTPPH-2. Expression of NTPPH-2 is accomplished by subcloning the cDNAs into appropriate vectors and transforming the vectors into host cells. In this case, the cloning vector was used to express NTPPH-2 in the baculovirus Fast-BAC system (GIBCO/BRL). Upstream of the cloning site, this vector contains a promoter for polyhedron coat protein. Infection of an insect cell line such as SF9 with the recombinant baculovirus results in the expression of NTPPH-2. Signal residues direct the secretion of NTPPH-2 into the culture media which can be used directly in the following assay for activity.

XI Demonstration of NTPPH-2 Activity

Human nucleotide pyrophosphohydrolase-2 activity is analyzed using thymidine monophosphate paranitrophenyl ester or [$^{32}$P] gamma labeled ATP as substrate. Media are chromatographed and peak fractions are analyzed kinetically as described in Cardenal, A. et al. (1996; Arthritis Rheum. 39:252–256.)

XII Production of NTPPH-2 Specific Antibodies

The amino acid sequence deduced from the cDNA encoding NTPPH-2 is analyzed using DNASTAR software (DNASTAR, Inc.) to determine regions of high immunogenicity and a corresponding oligopeptide is synthesized and used to raise anti-NTPPH-2 antibodies. The selection of appropriate peptide sequences and the techniques for antibody production can occur by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester. (MBS; Ausubel et al., supra.) Rabbits are immunized with the oligopeptide-KLH complex in complete Freund's adjuvant. The resulting antisera are tested for antipeptide activity, e.g., by binding the peptide to plastic, blocking with 1% BSA, reacting with rabbit antisera, washing, and reacting with radio iodinated, goat anti-rabbit IgG.

XIII Purification of Naturally Occurring NTPPH-2 Using Specific Antibodies

Naturally occurring or recombinant NTPPH-2 is substantially purified by immunoaffinity chromatography using antibodies specific for NTPPH-2. An immunoaffinity column is constructed by covalently coupling NTPPH-2 antibody to an activated chromatographic resin, such as CNBr-activated Sepharose (Pharmacia & Upjohn). After the coupling, the resin is blocked and washed according to the manufacturer's instructions.

Media containing NTPPH-2 is passed over the immunoaffinity column, and the column is washed under conditions that allow the preferential absorbance of NTPPH-2 (e.g., high ionic strength buffers in the presence of detergent). The column is eluted under conditions that disrupt antibody/NTPPH-2 binding (eg, a buffer of pH 2–3 or a high concentration of a chaotrope, such as urea or thiocyanate ion), and NTPPH-2 is collected.

XIV Identification of Molecules Which Interact with NTPPH-2

NTPPH-2 or biologically active fragments thereof are labeled with $^{125}$I Bolton-Hunter reagent. (Bolton, et al. (1973) Biochem. J. 133: 529.) Candidate molecules previously arrayed in the wells of a multi-well plate are incubated with the labeled NTPPH-2, washed and any wells with labeled NTPPH-2 complex are assayed. Data obtained using different concentrations of NTPPH-2 are used to calculate values for the number, affinity, and association of NTPPH-2 with the candidate molecules.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A substantially purified human nucleotide pyrophosphohydrolase-2 (NTPPH-2) comprising the amino acid sequence of SEQ ID NO:1 or a fragment of SEQ ID NO:1 having nucleotide pyrophosphohydrolase catalytic activity.

2. A substantially purified human nucleotide pyrophosphohydrolase-2 (NTPPH-2) having catalytic activity and at least 95% amino acid identity to the amino acid sequence of SEQ ID NO:1.

3. A composition comprising the NTPPH-2 of claim 1 and a suitable pharmaceutical carrier.

4. A method for screening a library of small molecules to identify a molecule which binds NTPPH-2, the method comprising the steps of:

(a) combining the library of small molecules with the NTPPH-2 of claim 1 under suitable conditions for complex formation; and (b) detecting complex formation, wherein the presence of the complex identifies a small molecule which binds NTPPH-2.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 1156 amino acids
      (B) TYPE: amino acid
      (C) STRANDEDNESS: single
      (D) TOPOLOGY: linear (vii) IMMEDIATE SOURCE:
      (A) LIBRARY: SATPF1008
      (B) CLONE: 1388013

(xi) SEQUENCE DESCRIPTION: SEQ ID NO: 1:

Met Ala Ser Leu Leu Pro Leu Leu Cys Leu Cys Val Val Ala Ala His
1               5                   10                  15

Leu Ala Gly Ala Arg Asp Ala Thr Pro Thr Glu Glu Pro Met Ala Thr
            20                  25                  30

-continued

```
Ala Leu Gly Leu Glu Arg Arg Ser Val Tyr Thr Gly Gln Pro Ser Pro
         35                  40                  45

Ala Leu Glu Asp Trp Glu Glu Ala Ser Glu Trp Thr Ser Trp Phe Asn
 50                  55                  60

Val Asp His Pro Gly Asp Gly Asp Phe Glu Ser Leu Ala Ala Ile
 65              70              75                  80

Arg Phe Tyr Tyr Gly Pro Ala Arg Val Cys Pro Arg Pro Leu Ala Leu
             85                  90                  95

Glu Ala Arg Thr Thr Asp Trp Ala Leu Pro Ser Ala Val Gly Glu Arg
             100                 105                 110

Val His Leu Asn Pro Thr Arg Gly Phe Trp Cys Leu Asn Arg Glu Gln
         115                 120                 125

Pro Arg Gly Arg Arg Cys Ser Asn Tyr His Val Arg Phe Arg Cys Pro
     130                 135                 140

Leu Glu Ala Ser Trp Gly Ala Trp Gly Pro Trp Gly Pro Cys Ser Gly
145                 150                 155                 160

Ser Cys Gly Pro Gly Arg Arg Leu Arg Arg His Cys Pro Ser Pro
                 165                 170                 175

Ala Gly Asp Ala Cys Pro Gly Arg Pro Leu Glu Ala Gln Lys Cys Val
             180                 185                 190

Arg Pro Arg Cys Pro Gly Cys Ser Leu Asp Thr Cys Glu Cys Pro Asp
         195                 200                 205

His Ile Leu Leu Gly Ser Val Val Thr Pro Ser Gly Gln Pro Leu Leu
     210                 215                 220

Gly Ala Arg Val Ser Leu Arg Asp Gln Pro Gly Thr Val Ala Thr Ser
225                 230                 235                 240

Asp Ala His Gly Thr Phe Arg Val Pro Gly Val Cys Ala Asp Ser Arg
                 245                 250                 255

Ala Asn Ile Arg Ala Gln Met Asp Gly Phe Ser Ala Gly Glu Ala Gln
             260                 265                 270

Ala Gln Ala Asn Gly Ser Ile Ser Val Val Thr Ile Ile Leu Asp Lys
         275                 280                 285

Leu Glu Lys Pro Tyr Leu Val Lys His Pro Glu Ser Arg Val Arg Glu
     290                 295                 300

Ala Gly Gln Asn Val Thr Phe Cys Cys Lys Ala Ser Gly Thr Pro Met
305                 310                 315                 320

Pro Lys Lys Tyr Ser Trp Phe His Asn Gly Thr Leu Leu Asp Arg Arg
                 325                 330                 335

Ala His Gly Tyr Gly Ala His Leu Glu Leu Arg Gly Leu Arg Pro Asp
             340                 345                 350

Gln Ala Gly Ile Tyr His Cys Lys Ala Trp Asn Glu Ala Gly Ala Val
         355                 360                 365

Arg Ser Gly Thr Ala Arg Leu Thr Val Leu Ala Pro Gly Gln Pro Ala
     370                 375                 380

Cys Asp Pro Arg Pro Arg Glu Tyr Leu Ile Lys Leu Pro Glu Asp Cys
385                 390                 395                 400

Gly Gln Pro Gly Ser Gly Pro Ala Tyr Leu Asp Val Gly Leu Cys Pro
                 405                 410                 415

Asp Thr Arg Cys Pro Ser Leu Ala Gly Ser Ser Pro Arg Cys Gly Asp
             420                 425                 430

Ala Ser Ser Arg Cys Cys Ser Val Arg Arg Leu Glu Arg Glu Ile
         435                 440                 445
```

```
His Cys Pro Gly Tyr Val Leu Pro Val Lys Val Val Ala Glu Cys Gly
    450                 455                 460

Cys Gln Lys Cys Leu Pro Pro Arg Gly Leu Val Arg Gly Arg Val Val
465                 470                 475                 480

Ala Ala Asp Ser Gly Glu Pro Leu Arg Phe Ala Arg Ile Leu Leu Gly
                485                 490                 495

Gln Glu Pro Ile Gly Phe Thr Ala Tyr Gln Gly Asp Phe Thr Ile Glu
            500                 505                 510

Val Pro Pro Ser Thr Gln Arg Leu Val Val Thr Phe Val Asp Pro Ser
        515                 520                 525

Gly Glu Phe Met Asp Ala Val Arg Val Leu Pro Phe Asp Pro Arg Gly
    530                 535                 540

Ala Gly Val Tyr His Glu Val Lys Ala Met Arg Lys Lys Ala Pro Val
545                 550                 555                 560

Ile Leu His Thr Ser Gln Ser Asn Thr Ile Pro Leu Gly Glu Leu Glu
                565                 570                 575

Asp Glu Ala Pro Leu Gly Glu Leu Val Leu Pro Ser Gly Ala Phe Arg
            580                 585                 590

Arg Ala Asp Gly Lys Pro Tyr Ser Gly Pro Val Glu Ala Arg Val Thr
        595                 600                 605

Phe Val Asp Pro Arg Asp Leu Thr Ser Ala Ala Ser Ala Pro Ser Asp
    610                 615                 620

Leu Arg Phe Val Asp Ser Asp Gly Glu Leu Ala Pro Leu Arg Thr Tyr
625                 630                 635                 640

Gly Met Phe Ser Val Asp Leu Arg Ala Pro Gly Ser Ala Glu Gln Leu
                645                 650                 655

Gln Val Gly Pro Val Ala Val Arg Val Ala Ala Ser Gln Ile His Met
            660                 665                 670

Pro Gly His Val Glu Ala Leu Lys Leu Trp Ser Leu Asn Pro Glu Thr
        675                 680                 685

Gly Leu Trp Glu Glu Ser Gly Phe Arg Arg Glu Gly Ser Ser Gly
    690                 695                 700

Pro Arg Val Arg Arg Glu Glu Arg Val Phe Leu Val Gly Asn Val Glu
705                 710                 715                 720

Ile Arg Glu Arg Arg Leu Phe Asn Leu Asp Val Pro Glu Arg Arg Arg
                725                 730                 735

Cys Phe Val Lys Val Arg Ala Tyr Ala Asn Asp Lys Phe Thr Pro Ser
            740                 745                 750

Glu Gln Val Glu Gly Val Val Thr Leu Val Asn Leu Glu Pro Ala
        755                 760                 765

Pro Gly Phe Ser Ala Asn Pro Arg Ala Trp Gly Arg Phe Asp Ser Ala
    770                 775                 780

Val Thr Gly Pro Asn Gly Ala Cys Leu Pro Ala Phe Cys Asp Ala Asp
785                 790                 795                 800

Arg Pro Asp Ala Tyr Thr Ala Leu Val Thr Ala Thr Leu Gly Gly Glu
                805                 810                 815

Glu Leu Glu Pro Ala Pro Ser Leu Pro Arg Pro Leu Pro Ala Thr Val
            820                 825                 830

Gly Val Thr Gln Pro Tyr Leu Asp Arg Leu Gly Tyr Arg Arg Thr Asp
        835                 840                 845

His Asp Asp Pro Ala Phe Lys Arg Asn Gly Phe Arg Ile Asn Leu Ala
    850                 855                 860

Lys Pro Arg Pro Gly Asp Pro Ala Glu Ala Asn Gly Pro Val Tyr Pro
```

-continued

```
                865                 870                 875                 880
Trp Arg Ser Leu Arg Glu Cys Gln Gly Ala Pro Val Thr Ala Ser His
                    885                 890                 895

Phe Arg Phe Ala Arg Val Glu Ala Asp Lys Tyr Glu Tyr Asn Val Val
                900                 905                 910

Pro Phe Arg Glu Gly Thr Pro Ala Ser Trp Thr Gly Asp Leu Leu Ala
                915                 920                 925

Trp Trp Pro Asn Pro Gln Glu Phe Arg Ala Cys Phe Leu Lys Val Lys
            930                 935                 940

Ile Gln Gly Pro Gln Glu Tyr Met Val Arg Ser His Asn Ala Gly Gly
945                 950                 955                 960

Ser His Pro Arg Thr Arg Gly Gln Leu Tyr Gly Leu Arg Asp Ala Arg
                965                 970                 975

Ser Val Arg Asp Pro Glu Arg Pro Gly Thr Ser Ala Ala Cys Val Glu
                980                 985                 990

Phe Lys Cys Ser Gly Met Leu Phe Asp Gln Arg Gln Val Asp Arg Thr
                995                 1000                1005

Leu Val Thr Ile Met Pro Gln Gly Ser Cys Arg Arg Val Ala Val Asn
    1010                1015                1020

Gly Leu Leu Arg Asp Tyr Leu Thr Arg His Pro Pro Val Pro Ala
025                 1030                1035                1040

Glu Asp Pro Ala Ala Phe Ser Met Leu Ala Pro Leu Asp Pro Leu Gly
                1045                1050                1055

His Asn Tyr Gly Val Tyr Thr Val Thr Asp Gln Ser Pro Arg Leu Ala
                1060                1065                1070

Lys Glu Ile Ala Ile Gly Arg Cys Phe Asp Gly Ser Ser Asp Gly Phe
    1075                1080                1085

Ser Arg Glu Met Lys Ala Asp Ala Gly Thr Ala Val Thr Phe Gln Cys
    1090                1095                1100

Arg Glu Pro Pro Ala Gly Arg Pro Ser Leu Phe Gln Arg Leu Leu Glu
105                 1110                1115                1120

Ser Pro Ala Thr Ala Leu Gly Asp Ile Arg Arg Glu Met Ser Glu Ala
                1125                1130                1135

Ala Gln Ala Gln Ala Arg Ala Ser Gly Pro Leu Arg Thr Arg Arg Gly
            1140                1145                1150

Arg Val Arg Gln
        1155

(2) INFORMATION FOR SEQ ID NO: 2:

(i) SEQUENCE CHARACTERISTICS:
        (A) LENGTH: 4183 base pairs
        (B) TYPE: nucleic acid
        (C) STRANDEDNESS: single
        (D) TOPOLOGY: linear (vii) IMMEDIATE SOURCE:
        (A) LIBRARY: SATPF1008
        (B) CLONE: 1388013

(xi) SEQUENCE DESCRIPTION: SEQ ID NO: 2:

GCCCGAGCAC GCCGCGGAGC CCGGACCTCC CTCGGACGCT CTGCCCCGGC CATGGCGTCG      60

CTGCTGCCAC TGCTCTGTCT CTGTGTCGTC GCTGCGCACC TGGCGGGGGC CCGAGACGCC     120

ACCCCCACCG AGGAGCCAAT GGCGACTGCA CTGGGCCTGG AAAGACGGTC CGTGTACACC     180

GGCCAGCCCT CACCAGCCCT GGAGGACTGG GAAGAGGCCA GCGAGTGGAC GTCCTGGTTC     240
```

```
AACGTGGACC ACCCCGGAGG CGACGGCGAC TTCGAGAGCC TGGCTGCCAT CCGCTTCTAC    300
TACGGGCCAG CGCGCGTGTG CCCGCGACCG CTGGCGCTGG AGGCGCGCAC CACGGACTGG    360
GCCCTGCCGT CCGCCGTCGG CGAGCGCGTG CACTTGAACC CCACGCGCGG CTTCTGGTGC    420
CTCAACCGCG AGCAACCGCG TGGCCGCCGC TGCTCCAACT ACCACGTGCG CTTCCGCTGC    480
CCACTAGAAG CCTCGTGGGG CGCGTGGGGC CGTGGGGTC CCTGCTCGGG GAGCTGTGGG    540
CCAGGCCGTC GCTTGCGCCG CCGCCACTGC CCAAGCCCCG CTGGGGATGC GTGTCCCGGG    600
CGTCCTCTGG AGGCGCAGAA GTGCGTGCGG CCTCGGTGTC CAGGGTGCAG CCTTGACACC    660
TGTGAATGCC CGGACCACAT CCTCCTGGGC TCGGTGGTCA CCCCATCTGG GCAACCACTG    720
CTAGGAGCCA GGGTCTCCCT GCGAGACCAG CCTGGCACTG TGGCCACCAG CGATGCTCAC    780
GGAACCTTCC GGGTGCCTGG TGTCTGTGCT GACAGCCGCG CCAACATCAG GGCCCAGATG    840
GATGGCTTCT CTGCAGGGGA GGCCCAGGCC CAGGCCAACG GATCCATCTC TGTGGTCACC    900
ATCATCCTTG ATAAGTTGGA GAAGCCGTAC CTGGTGAAAC ACCCTGAGTC CCGAGTGCGA    960
GAGGCTGGCC AGAATGTGAC TTTCTGCTGC AAAGCCTCCG GACCCCCAT GCCCAAGAAA   1020
TACTCCTGGT TCCACAATGG GACCCTGCTG GACAGGCGAG CTCATGGGTA CGGGGCCCAC   1080
CTGGAGCTSC GGGGACTGCG CCCAGACCAG GCTGGCATCT ACCACTGCAA GGCATGGAAT   1140
GAGGCGGGTG CCGTGCGCTC GGGCACTGCC CGGCTCACTG TACTTGCCCC AGGCCAGCCA   1200
GCCTGCGACC CCCGGCCCCG AGAGTACCTG ATCAAGCTCC CTGAGGACTG TGGTCAGCCA   1260
GGTAGTGGCC CTGCCTACCT GGATGTGGGC CTCTGTCCCG ACACCCGCTG CCCCAGCCTG   1320
GCAGGCTCCA GCCCCGCTG CGGGGACGCC AGCTCCCGCT GCTGCTCTGT GCGCCGTCTG   1380
GAGAGAAGGG AGATTCACTG CCCTGGCTAC GTCCTCCCAG TGAAGGTGGT GGCAGAGTGT   1440
GGCTGCCAGA AGTGTCTGCC CCCTCGGGGG CTGGTCCGGG GCCGTGTTGT GGCTGCTGAC   1500
TCCGGGGAGC CGCTACGCTT CGCCAGGATT CTGCTGGGCC AGGAGCCCAT CGGCTTCACC   1560
GCCTACCAGG GCGACTTTAC CATTGAGGTG CCGCCCTCCA CCCAGCGGCT GGTGGTGACT   1620
TTTGTGGACC CCAGCGGTGA GTTCATGGAC GCTGTCCGGG TCTTGCCTTT TGATCCTCGA   1680
GGTGCCGGCG TGTACCACGA GGTCAAGGCC ATGCGGAAGA AAGCCCCGGT CATTTTACAT   1740
ACCAGCCAGA GCAACACGAT CCCCCTGGGC GAGCTGGAAG ATGAGGCGCC CCTGGGCGAG   1800
CTGGTCCTGC CTTCTGGCGC TTTCCGCAGA GCCGACGGCA AACCCTACTC GGGGCCTGTG   1860
GAGGCCCGGG TGACGTTCGT GGACCCCCGA GACCTCACCT CGGCGGCGTC TGCCCCCAGT   1920
GACCTGCGCT TCGTGGACAG CGACGGCGAG CTGGCTCCAC TGCGCACCTA CGGCATGTTC   1980
TCCGTGGACC TCCGTGCGCC CGGCTCCGCG GAGCAGCTGC AGGTGGGGCC GGTGGCCGTG   2040
CGGGTGGCCG CCAGCCAGAT CCACATGCCA GGCCACGTGG AGGCCCTCAA GCTGTGGTCG   2100
CTGAACCCCG AGACCGGCTT GTGGGAGGAG GAGAGCGGCT TCCGGCGCGA GGGGTCCTCG   2160
GGCCCCCGGG TGCGCCGGGA GGAGCGCGTC TTCCTGGTGG CAACGTGGA GATCCGGGAG   2220
CGGCGCCTGT TCAATCTGGA CGTGCCTGAG CGCCGCCGCT GCTTCGTGAA GGTGCGCGCC   2280
TACGCCAACG ACAAGTTCAC CCCCAGCGAG CAGGTGGAGG GCGTGGTGGT CACGCTGGTC   2340
AATCTGGAGC CCGCCCCCGG CTTCTCCGCC AACCCCGTG CCTGGGGCCG CTTTGACAGC   2400
GCGGTCACCG GCCCCAATGG CGCCTGCCTC CCCGCCTTCT GCGACGCCGA CAGGCCAGAC   2460
GCCTACACCG CCCTGGTCAC CGCCACCCTG GGCGGCGAGG AGCTGGAGCC GGCCCCTTCC   2520
TTGCCCCGCC CACTCCCGGC CACCGTGGGC GTCACCCAGC CCTACCTGGA CAGGCTGGGG   2580
TACCGTCGGA CGGACCACGA CGATCCCGCC TTCAAGCGTA ACGGCTTCCG CATCAACCTC   2640
```

-continued

```
GCCAAGCCCA GGCCAGGTGA CCCCGCCGAG GCCAATGGGC CTGTGTACCC GTGGCGCAGC   2700

CTGCGGGAAT GCCAGGGGGC CCCGGTGACT GCCAGCCACT TCCGCTTCGC CAGGGTGGAG   2760

GCGGACAAGT ACGAGTACAA CGTGGTCCCC TTCCGAGAGG GCACACCTGC CTCCTGGACT   2820

GGCGATCTCC TGGCCTGGTG GCCCAACCCG CAGGAGTTCC GGGCCTGCTT CCTCAAGGTG   2880

AAGATCCAGG GTCCCCAGGA GTATATGGTC CGCTCCCACA ACGCAGGGGG CAGCCACCCA   2940

CGCACCCGCG GCCAGCTCTA CGGACTTCGG GATGCCCGGA GTGTGCGAGA CCCCGAGCGT   3000

CCGGGCACCT CGGCAGCCTG CGTGGAGTTC AAGTGCAGCG GGATGCTGTT CGACCAGCGG   3060

CAGGTGGACA GGACGCTGGT GACCATTATG CCCCAGGGCA GCTGCCGGCG CGTGGCCGTC   3120

AACGGACTCC TTCGGGATTA CCTGACCCGG CACCCCCCAC CGGTGCCCGC GGAGGACCCA   3180

GCTGCCTTCT CCATGCTGGC CCCCCTAGAC CCTCTGGGCC ACAACTATGG CGTCTACACT   3240

GTCACTGACC AGAGCCCACG CTTGGCCAAG GAGATCGCCA TTGGCCGCTG CTTTGATGGT   3300

TCCTCTGACG GYTTCTCCAG AGAGATGAAG GCTGATGCCG GCACAGCCGT CACCTTCCAG   3360

TGCCGGGAGC CACCGGCCGG ACGACCCAGC CTCTTCCAGA GGCTGCTGGA GTCCCCGGCG   3420

ACAGCACTTG GTGACATCCG CAGGGAGATG AGCGAGGCGG CGCAGGCACA GGCCCGGGCC   3480

TCAGGTCCCC TCCGCACCCG CCGGGGTAGG GTCCGGCAGT GACCTGGGCA GGGGCCTCGC   3540

TTTCCCACCT CCCTCCAGAC TCCTTTGACC CCAGGAAGTT TTGCCCCTCC TTCTTCTCCA   3600

GACAGCCCCC TCCCCAGGTG TCTGGGTCCC CTTTCCCGCC CCTTTCCAGA ACTCAGAGTC   3660

AGACAAGAAC CCAGAGCATC CGATGGTAGA ACACCAGGA  AGACAATTGT TGCTGTGTGG   3720

TATGGAATGG AGTTTGCGGT GACTCTGGGG CCAGCACCCA GGGACGACG  TTCAACCCTA   3780

GCCTGAAGGG ACCCGCTCCC AGCTCAGAAG CCGTCTCTGA CTTCTCGTGC GTATTTTGAC   3840

CCTGATTTCA ATCTTCTACC CTTGGGAGTT CTGGCGTTTG GCACAAAGTC CCCTCTGCCT   3900

GTTTGGAGCT CAGTGCTAGA CCAGGTCCCC TGCCCCGAGC TTTGTTTTTG GGGTTATTTA   3960

TTGAAACAAA GTGTGGGGAG CTGGTTGTGG GTGTGAGTGG GGGTGTGGGG TCCAGGCTGG   4020

GCCCAGTGAA AAGGAGGAAG GGGTTCCCAT GCGGGGAGG  CTCTGGGGCT GAGGGGAACA   4080

ATTCTCACGT GTTTGGTGCT TAGAGACCTG CCCGGGGCGT TGGGCAGGCC CTCCGGGGGC   4140

TGAATTAAAA ATGCTTTATT TCCAAAAAAA AAAAAAAAN  AAA                    4183
```

(2) INFORMATION FOR SEQ ID NO: 3:

(i) SEQUENCE CHARACTERISTICS:
        (A) LENGTH: 1156 amino acids
        (B) TYPE: amino acid
        (C) STRANDEDNESS: single
        (D) TOPOLOGY: linear (vii) IMMEDIATE SOURCE:
        (A) LIBRARY: SATPF1002
        (B) CLONE: 422069

(xi) SEQUENCE DESCRIPTION: SEQ ID NO: 3:

```
Met Ala Ser Leu Leu Pro Leu Leu Cys Leu Cys Val Val Ala Ala His
 1               5                  10                  15

Leu Ala Gly Ala Arg Asp Ala Thr Pro Thr Glu Glu Pro Met Ala Thr
            20                  25                  30

Ala Leu Gly Leu Glu Arg Arg Ser Val Tyr Thr Gly Gln Pro Ser Pro
        35                  40                  45

Ala Leu Glu Asp Trp Glu Glu Ala Ser Glu Trp Thr Ser Trp Phe Asn
    50                  55                  60
```

-continued

Val Asp His Pro Gly Gly Asp Gly Asp Phe Glu Ser Leu Ala Ala Ile
65                  70                  75                  80

Arg Phe Tyr Tyr Gly Pro Ala Arg Val Cys Pro Arg Pro Leu Ala Leu
            85                  90                  95

Glu Ala Arg Thr Thr Asp Trp Ala Leu Pro Ser Ala Val Gly Glu Arg
            100                 105                 110

Val His Leu Asn Pro Thr Arg Gly Phe Trp Cys Leu Asn Arg Glu Gln
            115                 120                 125

Pro Arg Gly Arg Arg Cys Ser Asn Tyr His Val Arg Phe Arg Cys Pro
    130                 135                 140

Leu Glu Ala Ser Trp Gly Ala Trp Gly Pro Trp Gly Pro Cys Ser Gly
145                 150                 155                 160

Ser Cys Gly Pro Gly Arg Arg Leu Arg Arg Arg His Cys Pro Ser Pro
                165                 170                 175

Ala Gly Asp Ala Cys Pro Gly Arg Pro Leu Glu Ala Gln Lys Cys Val
            180                 185                 190

Arg Pro Arg Cys Pro Gly Cys Ser Leu Asp Thr Cys Glu Cys Pro Asp
    195                 200                 205

His Ile Leu Leu Gly Ser Val Val Thr Pro Ser Gly Gln Pro Leu Leu
    210                 215                 220

Gly Ala Arg Val Ser Leu Arg Asp Gln Pro Gly Thr Val Ala Thr Ser
225                 230                 235                 240

Asp Ala His Gly Thr Phe Arg Val Pro Gly Val Cys Ala Asp Ser Arg
                245                 250                 255

Ala Asn Ile Arg Ala Gln Met Asp Gly Phe Ser Ala Gly Glu Ala Gln
            260                 265                 270

Ala Gln Ala Asn Gly Ser Ile Ser Val Val Thr Ile Ile Leu Asp Lys
    275                 280                 285

Leu Glu Lys Pro Tyr Leu Val Lys His Pro Glu Ser Arg Val Arg Glu
290                 295                 300

Ala Gly Gln Asn Val Thr Phe Cys Cys Lys Ala Ser Gly Thr Pro Met
305                 310                 315                 320

Pro Lys Lys Tyr Ser Trp Phe His Asn Gly Thr Leu Leu Asp Arg Arg
                325                 330                 335

Ala His Gly Tyr Gly Ala His Leu Glu Leu Arg Gly Leu Arg Pro Asp
            340                 345                 350

Gln Ala Gly Ile Tyr His Cys Lys Ala Trp Asn Glu Ala Gly Ala Val
    355                 360                 365

Arg Ser Gly Thr Ala Arg Leu Thr Val Leu Ala Pro Gly Gln Pro Ala
370                 375                 380

Cys Asp Pro Arg Pro Arg Glu Tyr Leu Ile Lys Leu Pro Glu Asp Cys
385                 390                 395                 400

Gly Gln Pro Gly Ser Gly Pro Ala Tyr Leu Asp Val Gly Leu Cys Pro
                405                 410                 415

Asp Thr Arg Cys Pro Ser Leu Ala Gly Ser Ser Pro Arg Cys Gly Asp
            420                 425                 430

Ala Ser Ser Arg Cys Cys Ser Val Arg Arg Leu Glu Arg Arg Glu Ile
    435                 440                 445

His Cys Pro Gly Tyr Val Leu Pro Val Lys Val Val Ala Glu Cys Gly
    450                 455                 460

Cys Gln Lys Cys Leu Pro Pro Arg Gly Leu Val Arg Gly Arg Val Val
465                 470                 475                 480

-continued

```
Ala Ala Asp Ser Gly Glu Pro Leu Arg Phe Ala Arg Ile Leu Leu Gly
            485                 490                 495

Gln Glu Pro Ile Gly Phe Thr Ala Tyr Gln Gly Asp Phe Thr Ile Glu
            500                 505                 510

Val Pro Pro Ser Thr Gln Arg Leu Val Val Thr Phe Val Asp Pro Ser
            515                 520                 525

Gly Glu Phe Met Asp Ala Val Arg Val Leu Pro Phe Asp Pro Arg Gly
    530                 535                 540

Ala Gly Val Tyr His Glu Val Lys Ala Met Arg Lys Lys Ala Pro Val
545                 550                 555                 560

Ile Leu His Thr Ser Gln Ser Asn Thr Ile Pro Leu Gly Glu Leu Glu
                565                 570                 575

Asp Glu Ala Pro Leu Gly Glu Leu Val Leu Pro Ser Gly Ala Phe Arg
            580                 585                 590

Arg Ala Asp Gly Lys Pro Tyr Ser Gly Pro Val Glu Ala Arg Val Thr
        595                 600                 605

Phe Val Asp Pro Arg Asp Leu Thr Ser Ala Ala Ser Ala Pro Ser Asp
    610                 615                 620

Leu Arg Phe Val Asp Ser Asp Gly Glu Leu Ala Pro Leu Arg Thr Tyr
625                 630                 635                 640

Gly Met Phe Ser Val Asp Leu Arg Ala Pro Gly Ser Ala Glu Gln Leu
                645                 650                 655

Gln Val Gly Pro Val Ala Val Arg Val Ala Ala Ser Gln Ile His Met
            660                 665                 670

Pro Gly His Val Glu Ala Leu Lys Leu Trp Ser Leu Asn Pro Glu Thr
        675                 680                 685

Gly Leu Trp Glu Glu Glu Ser Gly Phe Arg Arg Glu Gly Ser Ser Gly
    690                 695                 700

Pro Arg Val Arg Arg Glu Glu Arg Val Phe Leu Val Gly Asn Val Glu
705                 710                 715                 720

Ile Arg Glu Arg Arg Leu Phe Asn Leu Asp Val Pro Glu Arg Arg Arg
                725                 730                 735

Cys Phe Val Lys Val Arg Ala Tyr Ala Asn Asp Lys Phe Thr Pro Ser
            740                 745                 750

Glu Gln Val Glu Gly Val Val Thr Leu Val Asn Leu Glu Pro Ala
        755                 760                 765

Pro Gly Phe Ser Ala Asn Pro Arg Ala Trp Gly Arg Phe Asp Ser Ala
    770                 775                 780

Val Thr Gly Pro Asn Gly Ala Cys Leu Pro Ala Phe Cys Asp Ala Asp
785                 790                 795                 800

Arg Pro Asp Ala Tyr Thr Ala Leu Val Thr Ala Thr Leu Gly Gly Glu
                805                 810                 815

Glu Leu Glu Pro Ala Pro Ser Leu Pro Arg Pro Leu Pro Ala Thr Val
            820                 825                 830

Gly Val Thr Gln Pro Tyr Leu Asp Arg Leu Gly Tyr Arg Arg Thr Asp
        835                 840                 845

His Asp Asp Pro Ala Phe Lys Arg Asn Gly Phe Arg Ile Asn Leu Ala
    850                 855                 860

Lys Pro Arg Pro Gly Asp Pro Ala Glu Ala Asn Gly Pro Val Tyr Pro
865                 870                 875                 880

Trp Arg Ser Leu Arg Glu Cys Gln Gly Ala Pro Val Thr Ala Ser His
                885                 890                 895

Phe Arg Phe Ala Arg Val Glu Ala Asp Lys Tyr Glu Tyr Asn Val Val
```

-continued

```
                     900                 905                  910
Pro Phe Arg Glu Gly Thr Pro Ala Ser Trp Thr Gly Asp Leu Leu Ala
        915                 920                 925
Trp Trp Pro Asn Pro Gln Glu Phe Arg Ala Cys Phe Leu Lys Val Lys
    930                 935                 940
Ile Gln Gly Pro Gln Glu Tyr Met Val Arg Ser His Asn Ala Gly Gly
945                 950                 955                 960
Ser His Pro Arg Thr Arg Gly Gln Leu Tyr Gly Leu Arg Asp Ala Arg
                965                 970                 975
Ser Val Arg Asp Pro Glu Arg Pro Gly Thr Ser Ala Ala Cys Val Glu
                980                 985                 990
Phe Lys Cys Ser Gly Met Leu Phe Asp Gln Arg Gln Val Asp Arg Thr
            995                 1000                1005
Leu Val Thr Ile Met Pro Gln Gly Ser Cys Arg Arg Val Ala Val Asn
    1010                1015                1020
Gly Leu Leu Arg Asp Tyr Leu Thr Arg His Pro Pro Val Pro Ala
025                 1030                1035                1040
Glu Asp Pro Ala Ala Phe Ser Met Leu Ala Pro Leu Asp Pro Leu Gly
                1045                1050                1055
His Asn Tyr Gly Val Tyr Thr Val Thr Asp Gln Ser Pro Arg Leu Ala
            1060                1065                1070
Lys Glu Ile Ala Ile Gly Arg Cys Phe Asp Gly Ser Ser Asp Gly Phe
        1075                1080                1085
Ser Arg Glu Met Lys Ala Asp Ala Gly Thr Ala Val Thr Phe Gln Cys
    1090                1095                1100
Arg Glu Pro Pro Ala Gly Arg Pro Ser Leu Phe Gln Arg Leu Leu Glu
105                 1110                1115                1120
Ser Pro Ala Thr Ala Leu Gly Asp Ile Arg Arg Glu Met Ser Glu Ala
                1125                1130                1135
Ala Gln Ala Gln Ala Arg Ala Ser Gly Pro Leu Arg Thr Arg Arg Gly
            1140                1145                1150
Arg Val Arg Gln
    1155
```